US010585042B2

(12) United States Patent
Ünlü et al.

(10) Patent No.: US 10,585,042 B2
(45) Date of Patent: Mar. 10, 2020

(54) SYSTEMS AND METHODS FOR IMAGING MICROWELL PLATE SAMPLES

(71) Applicants: TRUSTEES OF BOSTON UNIVERSITY, Boston, MA (US); NANOVIEW BIOSCIENCES, INC., Brighton, MA (US)

(72) Inventors: M. Selim Ünlü, Newton, MA (US); Derin Sevenler, Boston, MA (US); Jacob Trueb, Arlington, MA (US); Oguzhan Avci, Boston, MA (US); Celalettin Yurdakul, Brighton, MA (US); Steven Scherr, Brookline, MA (US); George G. Daaboul, Watertown, MA (US); David S. Freedman, Newton Highlands, MA (US)

(73) Assignees: TRUSTEES OF BOSTON UNIVERSITY, Boston, MA (US); NANOVIEW BIOSCIENCES, INC., Brighton, MA (US)

( * ) Notice: Subject to any disclaimer, the term of this patent is extended or adjusted under 35 U.S.C. 154(b) by 0 days.

(21) Appl. No.: 16/432,376

(22) Filed: Jun. 5, 2019

(65) Prior Publication Data
US 2019/0376896 A1     Dec. 12, 2019

Related U.S. Application Data

(60) Provisional application No. 62/681,333, filed on Jun. 6, 2018.

(51) Int. Cl.
*G01N 21/64* (2006.01)
*B01L 3/00* (2006.01)

(52) U.S. Cl.
CPC .......... *G01N 21/6452* (2013.01); *B01L 3/508* (2013.01); *G01N 21/6458* (2013.01)

(58) Field of Classification Search
CPC .......... G01N 21/6452; G01N 21/6458; G01N 21/6456
See application file for complete search history.

(56) References Cited

U.S. PATENT DOCUMENTS

| 2012/0200694 A1* | 8/2012 | Garsha | G01N 21/6456 348/79 |
| 2013/0155499 A1 | 6/2013 | Dixon | |

(Continued)

OTHER PUBLICATIONS

SCIENION™ AG. Multiplexed ELISA of cardiovascular disease biomarkers in 96 wellplate. sciFLEX Arrayer; Application Note No. 08019, Sep. 2016. Retrieved from http://www.scienion.com/fileadmin/user_upload/pdf/08019_AppNote_19_Multiplex_ELISA_with_microarrays_in_96_well_plates_20170112.pdf (2 pages).

(Continued)

*Primary Examiner* — Yara B Green
(74) *Attorney, Agent, or Firm* — Nixon Peabody LLP

(57) ABSTRACT

A system for analyzing one or more liquid samples includes a microwell plate including a plurality of rows of wells configured to store liquid samples, a sensor array that is moveable relative to the microwell plate along a first axis between a first position and a second position to allow a portion of the sensor array to be disposed within a first one of the plurality of rows of wells when the sensor array is in the second position, an objective, and one or more linear translation stages configured to move the microwell plate relative to the objective (i) along a second axis that is orthogonal to the first axis, (ii) along a third axis that is orthogonal to the first axis and the second axis, or (iii) both (i) and (ii).

24 Claims, 14 Drawing Sheets

(56) References Cited

U.S. PATENT DOCUMENTS

2017/0131267 A1 5/2017 Lee
2017/0270690 A1 9/2017 Chung

OTHER PUBLICATIONS

Trune, D.R. et al.; "Simultaneous measurement of multiple ear proteins with multiplex elisa assays"; Hear Res. 2011; 275(1-2): 1-7 (15 pages).
Avci, O. et al.; "Interferometric reflectance imaging sensor (IRIS)—a Platform Technology for Multiplexed Diagnostics and Digital Detection"; Sensors, 2015; 15(7): 17649-17665. PCMID: PMC4541952 (17 pages).
Ozkumur, E. et al.; "Label-free microarray imaging for direct detection of DNA hybridization and single-nucleotide mismatches"; Biosens. Bioelectron. 2010; 25(7): 1789-1795. PMCID: PMC2824047 (15 pages).
Daaboul, G. et al.; "LED-based Interferometric Reflectance Imaging Sensor for quantitative dynamic monitoring of biomolecular interactions"; Biosens. Bioelectron. 2011; 26(5): 2221-2227 (7 pages).
Daaboul, G. et al.; "High-Throughput Detection and Sizing of Individual Low-Index Nanoparticles and Viruses for Pathogen Identification"; Nano. Lett. 2010; 10: 4727-4731. PMID: 20964282 (5 pages).
Daaboul, G. et al.; "Digital Sensing and Sizing of Vesicular Stomatitis Virus Pseudotypes in Complex Media; A Model for Ebola and Marburg detection"; ACS Nano. Jun. 24, 2014; 8(6): 6047-6055. PMCID: PMC4466106 (17 pages).
Daaboul, G. et al.; "Enhanced light microscopy visualization of virus particles from Zika virus to filamentous ebolaviruses"; PLoOne 12(6): e0179728; MBio. Jun. 26, 2017. Retrieved from https://doi.org/10.1371/journal.pone.0179728 (15 pages).
Daaboul, G. et al.; "Digital Detection of Exosomes by Interferometric Imaging"; Nature Sci. Rep. Nov. 17, 2016; 6: 37246. DOI: 10.1038. (10 pages).
Scherr, S.M. et al.; "Real-time Capture and Visualization of Individual Viruses in Complex Media"; ACS Nano. Feb. 23, 2016; 10(2): 2827-2833 (15 pages).
SwissCI; "96 Well Glass-bottom Plate" product specification; date unknown; retrieved from https://docs.wixstatic.com/ugd/ad9d93_8e8fde82980f468ba5f96fab016d0e37.pdf on Aug. 6, 2019 (1 page).
ThorLabs; "M660L4 660 nm Mounted LED" product specification; Dec. 8, 2015; retrieved from https://www.thorlabs.com/drawings/242ce4c06fde5e96-13FA8548-09CA-936E-EEC51AD10BFF718E/M660L4-SpecSheet.pdf (3 pages).
ThorLabs "Is200 Series Integrating Spheres" Specification Sheet, rev. F, May 31, 2010; retrieved from https://www.thorlabs.com/thorproduct.cfm?partnumber=IS200 (3 pages).
ThorLabs, "CM1-BS013 Non-Ploarizing Beamsplitter Cubes in 30 mm Cage Cubes" Specification Sheet, Sep. 27, 2016; retrieved from https://www.thorlabs.com/catalogpages/Obsolete/2016/CM1-BS013.pdf (10 pages).
ThorLabs; "Ring-Actuated SM-Threaded Iris Diaphragms" Specification Sheet; publication date unknown; retrieved from https://www.thorlabs.com/thorproduct.cfm?partnumber=SM1D12D on Aug. 6, 2019 (2 pages).
ThorLabs; "AC254-060-A-ML Achromatic Doublet" and "Mounted Achromatic Doublets, AR Coated: 400-700 nm" Specification Sheets; retrieved from https://www.thorlabs.com/newgrouppage9.cfm?objectgroup_id=2696&pn=AC254-030-A-ML#3441 on Aug. 6, 2019 (5 pages).
Thorlabs "SM1T10 Lens Tube Couplers" Specification Sheet; publication date unknown; retrieved from https://www.thorlabs.com/newgrouppage9.cfm?objectgroup_id=2704&pn=SM1T10#1526 on Aug. 6, 2019 (5 pages).
Extech Raymarine; "Grasshopper2 GigE" Specification Sheet; retrieved from https://www.flir.com/support/products/grasshopper2-gige#Specifications on Aug. 6, 2019 (3 pages).
Monroe, M.R. et al.; "Single Nanoparticle Detection for Multiplexed Protein Diagnostics with Attomolar Sensitivity in Serum and Unprocessed Whole Blood"; Anal. Chem. Apr. 2, 2013; 85(7): 3698-3706. PMCID: PMC3690328 (18 pages).
Nikon; "CFI Plan Flour 40X" product brochures; Dec. 2018; retrieved from https://www.nikon.com/products/microscope-solutions/support/download/brochures/#toc15 on Aug. 6, 2019 (28 pages).
Thorlabs; "Kinematic Platform 200B Mounts" Specification Sheet: retrieved from https://www.thorlabs.com/newgrouppage9.cfm?objectgroup_id=1811&pn=KM200B on Aug. 6, 2019 (5 pages).
International Search Report for Application No. PCT/US2019/035499, dated Oct. 9, 2019 (2 pages).
Written Opinion of International Searching Authority for Application No. PCT/US2019/035499, dated Oct. 9, 2019 (5 pages).

* cited by examiner

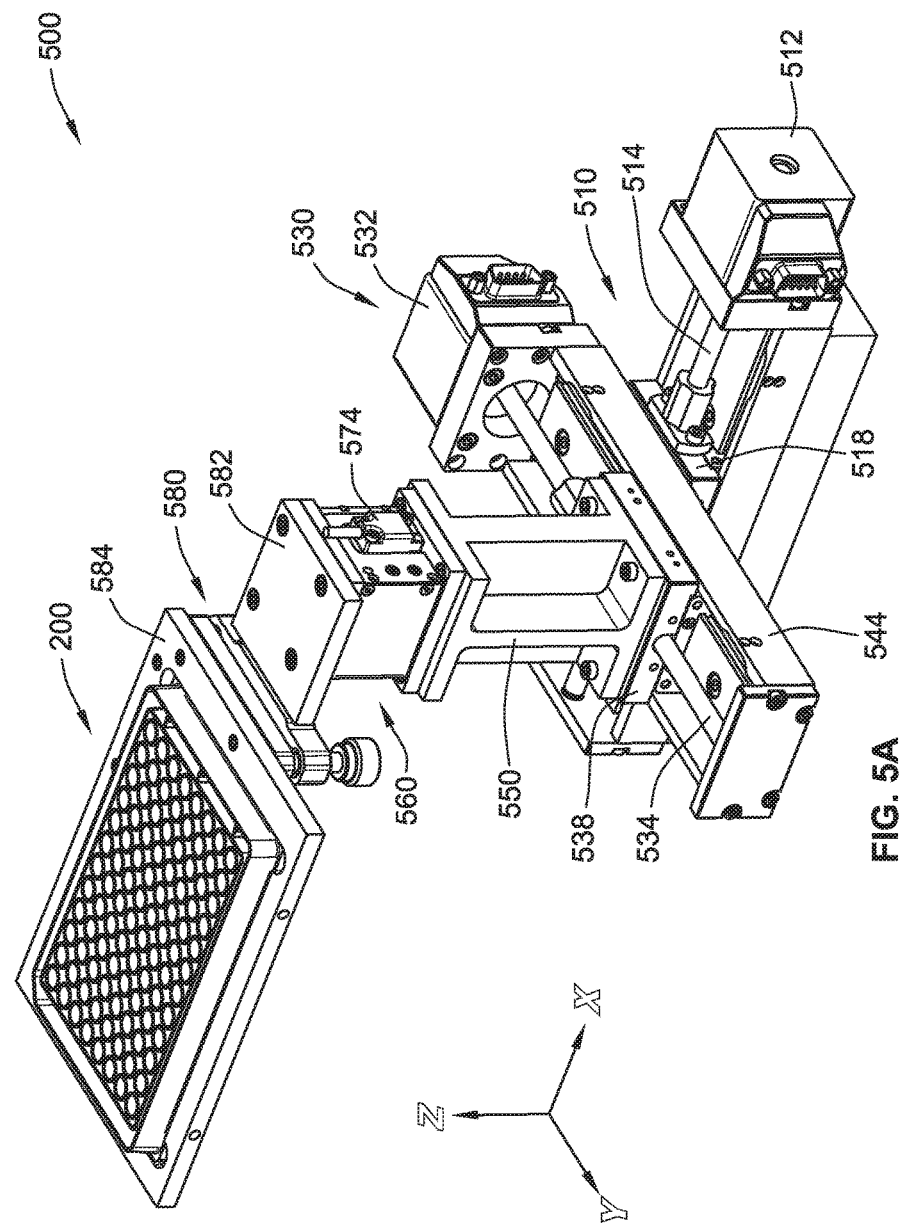

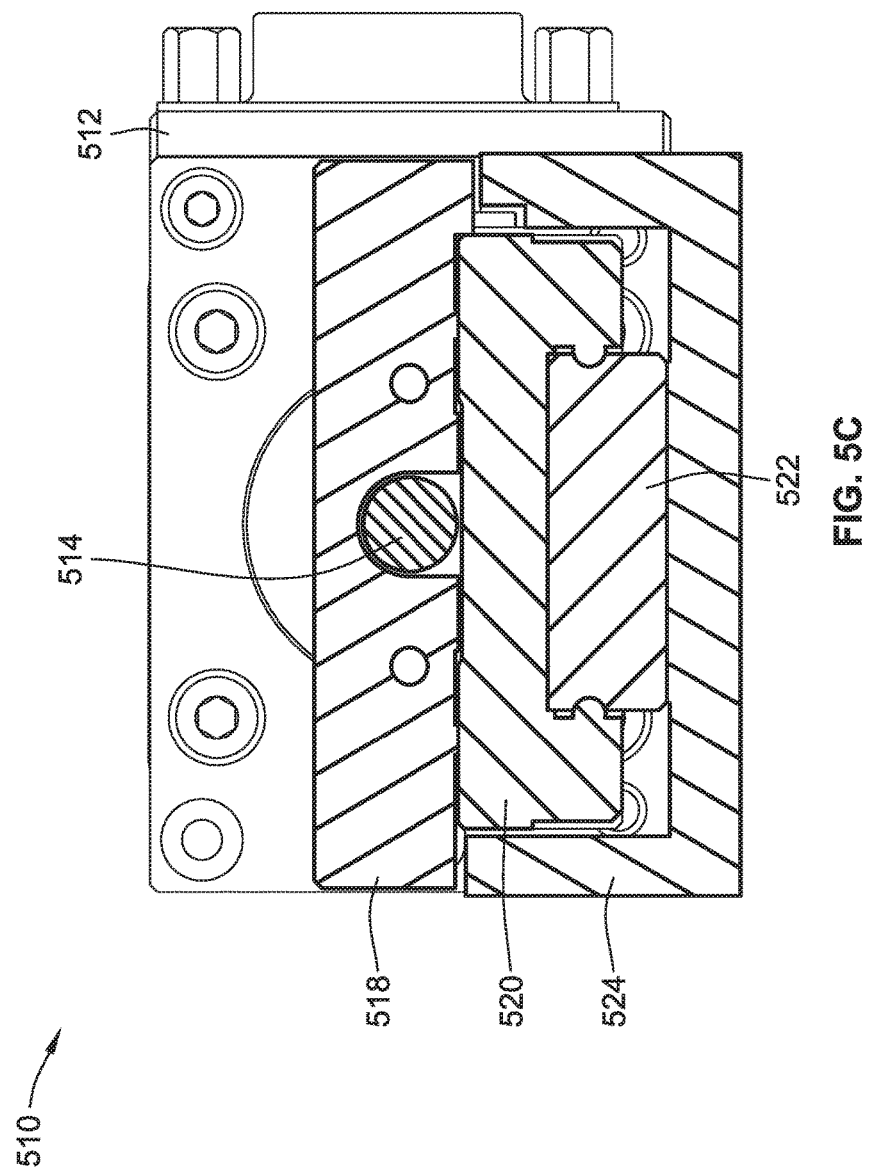

SYSTEMS AND METHODS FOR IMAGING MICROWELL PLATE SAMPLES

CROSS-REFERENCE TO RELATED APPLICATIONS

This application claims the benefit of and priority to U.S. Provisional Application No. 62/681,333, filed on Jun. 6, 2018, which is hereby incorporated by reference herein in its entirety.

TECHNICAL FIELD

The present disclosure relates generally to microscopy systems, and more particularly, to systems and methods for imaging one or more samples in a microwell plate.

BACKGROUND

Microwell plates (also known as microtiter plates) are often used in analytical research and clinical diagnostics. A microwell plate includes a plurality of sample wells (e.g., between 24 and 9,600 wells) containing liquid samples (e.g., incubated biological samples). Each sample well is analyzed by a plate reader system to detect specific biological events. However, prior systems and methods for analyzing the liquid samples in microwell plates suffer from tradeoffs between low-throughput multiplex analysis and high-throughput, non-multiplexed analysis. The present disclosure is directed to solving these and other problems.

SUMMARY

According to some implementations of the present disclosure, a system for analyzing one or more liquid samples includes a microwell plate including a plurality wells arranged in a plurality of rows, each of the plurality of wells having an upper opening and an opposing transparent lower surface, each of the plurality of wells being configured to store a liquid sample therein, a sensor array including a plurality of sensors, the sensor array being moveable relative to the microwell plate along a first axis between a first position and a second position, each of the plurality of sensors being positioned within a corresponding well at a predetermined depth for at least one of the plurality of rows responsive to the sensor array being in the second position, an objective, an imaging device, and one or more linear translation stages configured to move the microwell plate relative to the objective along (i) a second axis, (ii) a third axis, or (iii) both (i) and (ii) to allow the imaging device to obtain image data reproducible as one or more images of each of the plurality of sensors.

According to some implementations of the present disclosure, a system for analyzing one or more liquid samples includes a microwell plate including a plurality of rows of wells configured to store liquid samples, a sensor array that is moveable relative to the microwell plate along a first axis between a first position and a second position to allow a portion of the sensor array to be disposed within a first one of the plurality of rows of wells when the sensor array is in the second position, an objective, and one or more linear translation stages configured to move the microwell plate relative to the objective (i) along a second axis that is orthogonal to the first axis, (ii) along a third axis that is orthogonal to the first axis and the second axis, or (iii) both (i) and (ii).

According to some implementations of the present disclosure, a method for imaging one or more liquid samples disposed in a microwell plate includes moving a sensor array including a plurality of sensors from a first vertical position towards a second vertical position such that each of the plurality of sensors is disposed within a corresponding well in a first row of wells of the microwell plate, moving, using one or more linear translation stages, the microwell plate such that a first one of the plurality of sensors is positioned within a field of view of an objective, generating, using the objective and an imaging device, first image data reproducible as one or more images of the first sensor, moving, using the one or more linear translation stages, the microwell plate such that a second one of the plurality of sensors is positioned within the field of view of the objective, and generating, using the objective and the imaging device, second image data reproducible as one or more images of the second sensor.

The above summary is not intended to represent each embodiment or every aspect of the present invention. Additional features and benefits of the present invention are apparent from the detailed description and figures set forth below.

BRIEF DESCRIPTION OF THE DRAWINGS

FIG. 5A is a partial perspective view of the system of FIG. 1 including a translation stage sub-assembly according to some implementations of the present disclosure;

FIG. 5C is a cross-sectional view of the first linear translation stage of FIG. 5B according to some implementations of the present disclosure;

Figure 1:
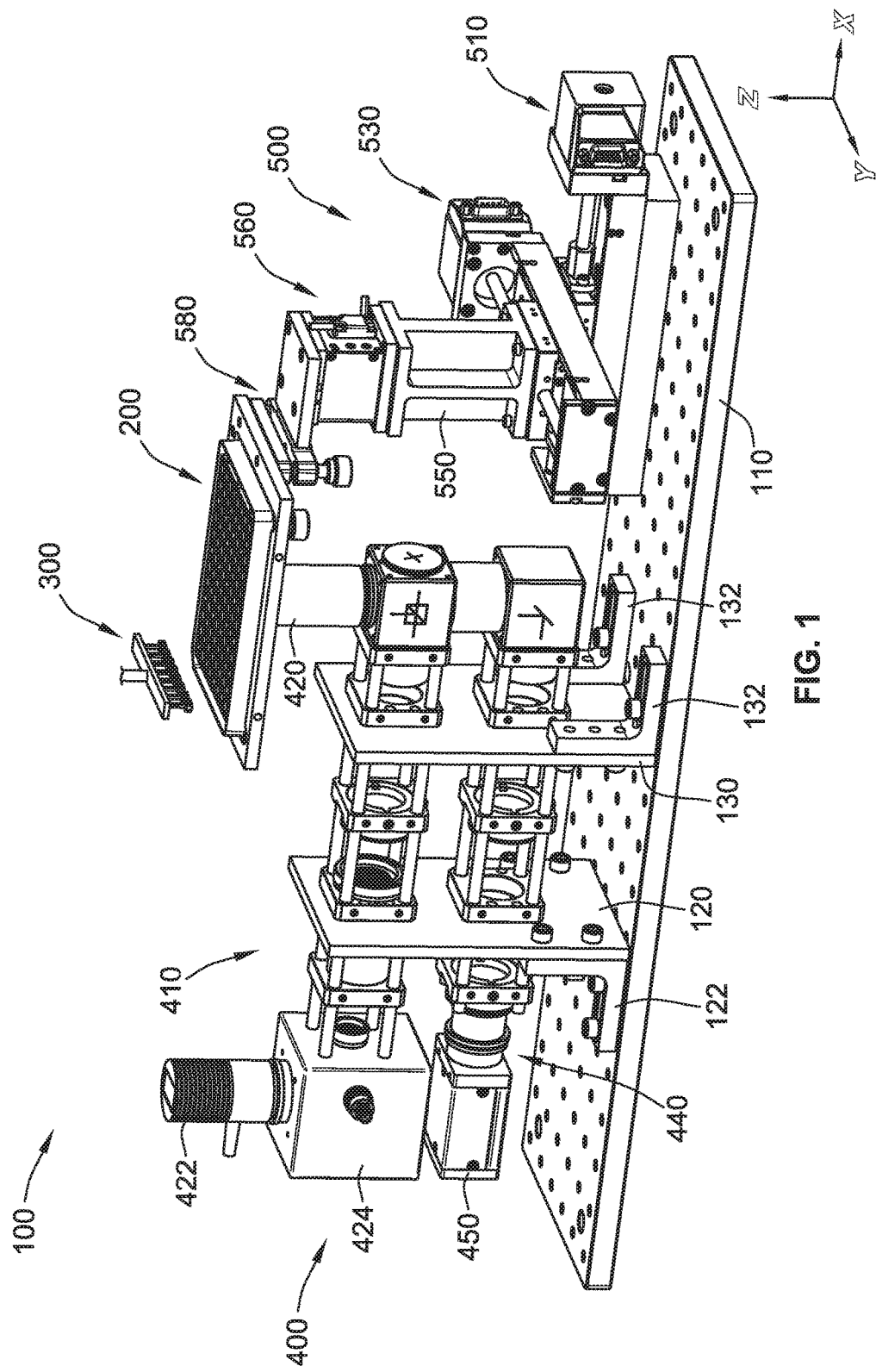
FIG. 1 is a perspective view of a system for imaging and analyzing one or more samples according to some implementations of the present disclosure.

While the disclosure is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

DETAILED DESCRIPTION

Microwell plates (also known as microplates or microtiter plates) are used in analytical research and clinical diagnostics (e.g., exosome detection and characterization, rapid quantitative and sensitive virus titers, and drug delivery nanoparticle characterization). To that end, each of the sample wells containing a sample liquid (e.g., biological sample) need to be analyzed. One type of biosensor system for analyzing microwell plates uses an array of functionalized optical fiber tips (e.g., ForteBio™) that are dipped into the sample wells. However, these types of systems are not multiplexed, meaning that the systems can only test each sample well with a single probe molecule species. Other types of systems are multiplexed and can test for many different molecule species in each sample well at one time (e.g., GE Biacore™ or Adarza AIR™), however, these systems have low-throughput. For example, a microwell plate containing many sample wells (e.g., hundreds or thousands) could take many hours or days to completely image and analyze using these systems. High-throughput capabilities would be desirable in the field of biomedical research.

Referring to FIG. 1, a system 100 for analyzing one or more liquid samples includes a microwell plate 200, a sensor array 300, a microscopy assembly 400, and a linear translation stage assembly 500. Generally, the system 100 uses the linear translation stage assembly 500 to move the microwell plate 200 relative to microscopy assembly 400 such that an objective 420 can capture one or more images of a portion of the sensor array 300 to analyze one or more samples (e.g., liquid samples) contained in the microwell plate 200. The system 100 allows for high-throughput imaging and analysis of the samples in the microwell plate 200. That is, the system 100 can image and analyze the samples many times faster than the conventional techniques discussed above (e.g., in a matter of hours compared to a matter of days for conventional techniques).

Figure 2A:
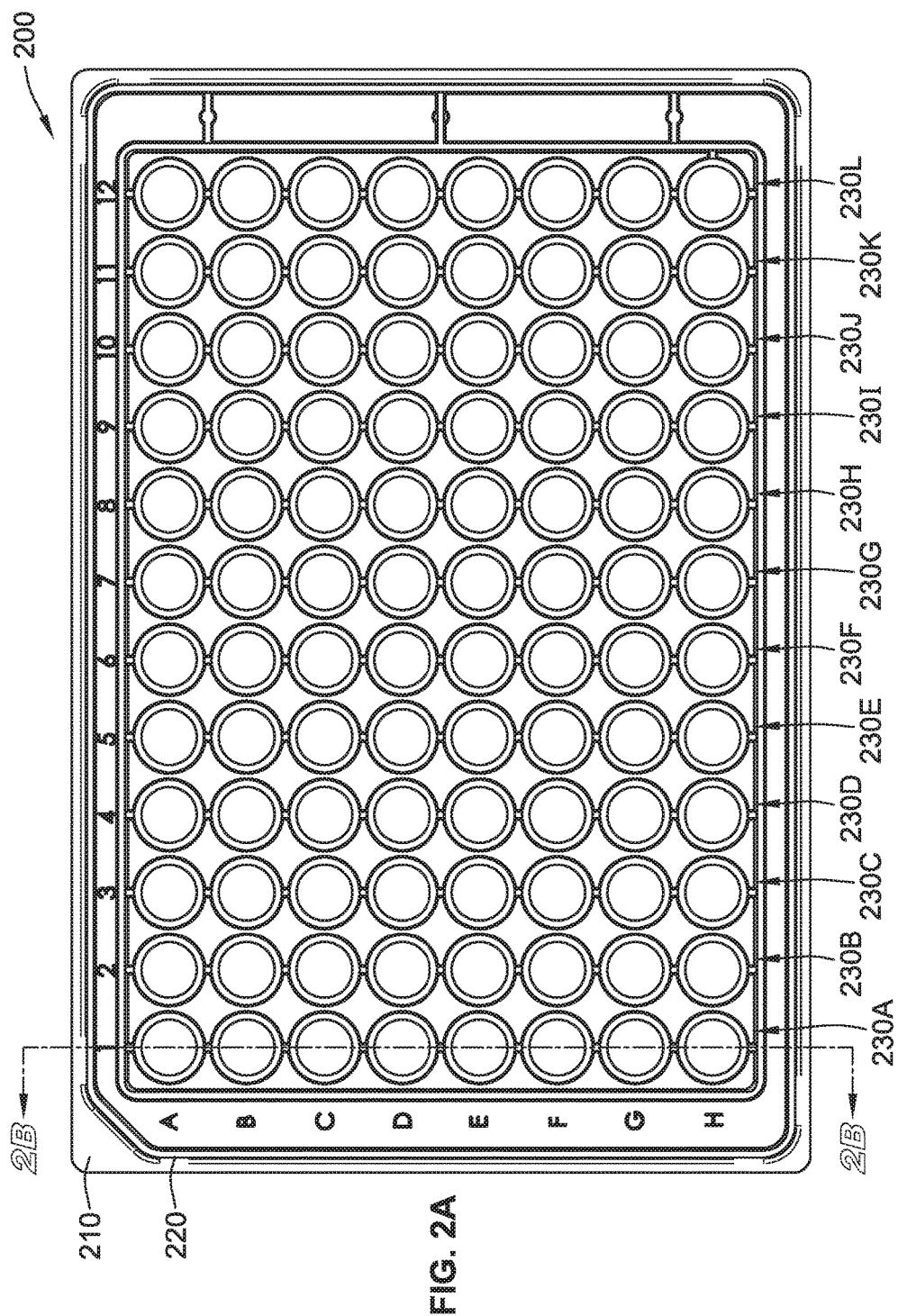
FIG. 2A is a top view of a microwell plate of the system of FIG. 1 according to some implementations of the present disclosure.
Figure 2B:
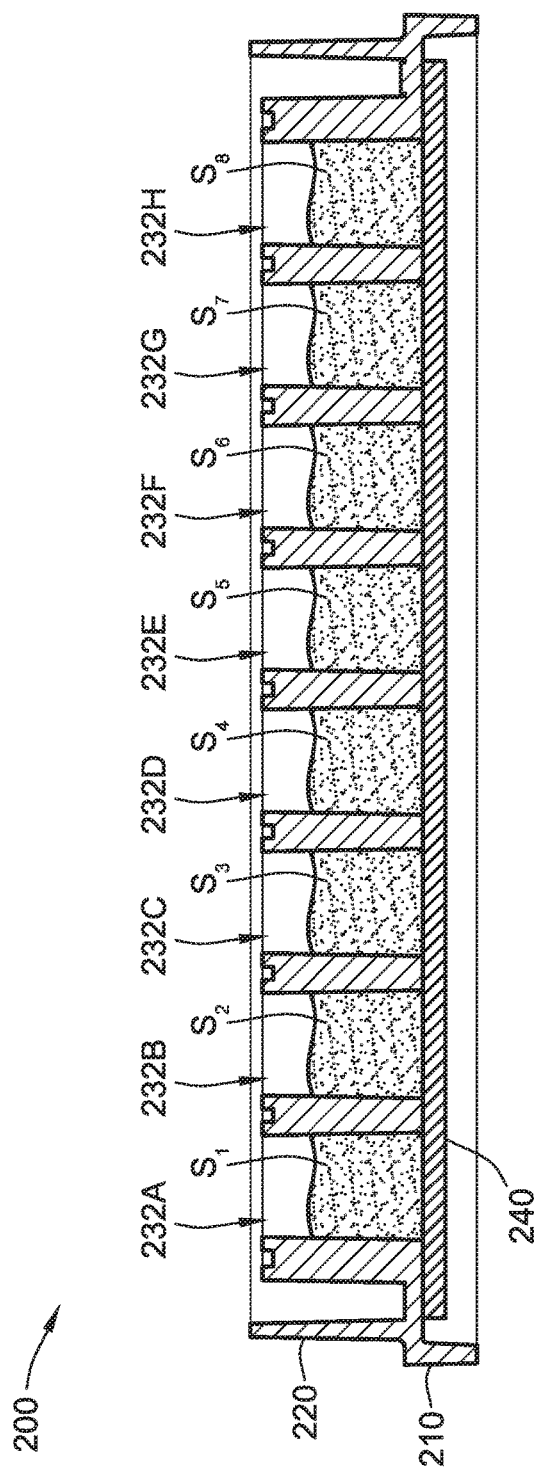
FIG. 2B is a side cross-sectional view of the microwell plate of FIG. 2A according to some implementations of the present disclosure.

Referring generally to FIGS. 2A and 2B, the microwell plate 200 includes a base portion 210, a sidewall 220, a plurality of rows of microwells ("wells") 230A-230L, and a glass plate 240 (FIG. 2B). As shown in FIG. 2A, each of the plurality of rows 230A-230L includes 8 wells. To keep the samples from flowing out of the wells, the microwell plate 200 includes glass plate 240, as shown in FIG. 2B. The glass plate 240 is transparent such that an objective of the microscopy system 400 (FIG. 1) can image portions of the sensor array 300 disposed within the plurality of rows 230A-230L, as described in further detail herein. As described in further detail below, the glass plate 240 (FIG. 2B) has one or more predetermined optical properties that allowed selection of an objective of the microscopy assembly 400 that is calibrated to account for the glass plate 240 being positioned between the objective and the sample.

As shown in FIG. 2B, row 230A includes a first well 232A storing a first sample $S_1$, a second well 232B storing a second sample $S_2$, a third well 232C storing a third sample $S_3$, a fourth well 232D storing a fourth sample $S_4$, a fifth well 232E storing a fifth sample $S_5$, a sixth well 232F storing a sixth sample $S_6$, a seventh well 232G storing a seventh sample $S_7$, and an eighth well 232H storing an eighth sample $S_8$. The liquid samples can be aspirated or dispensed from and to the microwell plate 200 manually or using a robotic system, for example. The samples $S_1$-$S_8$ within row 230A can be, for example, a biological sample, one or more target species (e.g., target biomolecules, target particles, or both), a buffer solution, a control solution, or any combination thereof. That is, each of the wells 232A-232G in row 230A can store the same sample (e.g., all wells store the same biological sample), the same type of sample (e.g., all wells store a biological sample, but not the same biological sample), or different types of samples (e.g., some wells in a row store a biological sample and some wells in the same row store a buffer solution). Moreover, the wells in each of the rows 230A-230L can store the same or different samples. For example, the wells in row 230A can store a first set of biological samples, the wells in 230B can store a buffer solution or a control solution, and the wells in row 230C can store a second set of biological samples.

Each well in rows 230A-230L of the microwell plate 200 can have a depth of, for example, between about 5 mm and about 25 mm, between about 8 mm and about 12 mm, or about 10 mm. In implementations where the wells in rows 230A-230L have a generally circular shape, the diameter of each well can be, for example, between about 3 mm and about 10 mm, between about 5 mm and about 8, between about 6 mm and about 7 mm, etc. Further, a center of each of the wells in rows 230A-230L can be spaced from a center of immediately adjacent wells by, for example, about 9 mm.

While the microwell plate 200 is shown and described herein as including 96 wells (12 rows and 8 wells per row), more generally, the microwell plate 200 can have between 24 wells and 9,600 wells, for example, or any other suitable number of wells. Preferably, the ratio of wells in a row to the total number of rows is 2:3. That is, the plurality of rows 230A-230L are arranged in a matrix where a first row of the matrix (e.g., row 230A) has a first number of wells that is a multiple of 2 (e.g., 8 wells) and a second row of the matrix that is orthogonal to the first row (e.g., orthogonal to row 230A) having a second number of wells that is a multiple of 3 (e.g., 12 wells). Further, while each of the wells in rows 230A-230L is shown in FIG. 2A as having a generally circular shape, in some implementations, the wells have a generally rectangular shape, a generally square shape, or any other suitable shape. In one exemplary, non-limiting implementation of the system 100, the microwell plate 200 is a SWISSCI 96 well glass bottom plate manufactured by SWISSCI AG of Zug, Switzerland.

Figure 3A:
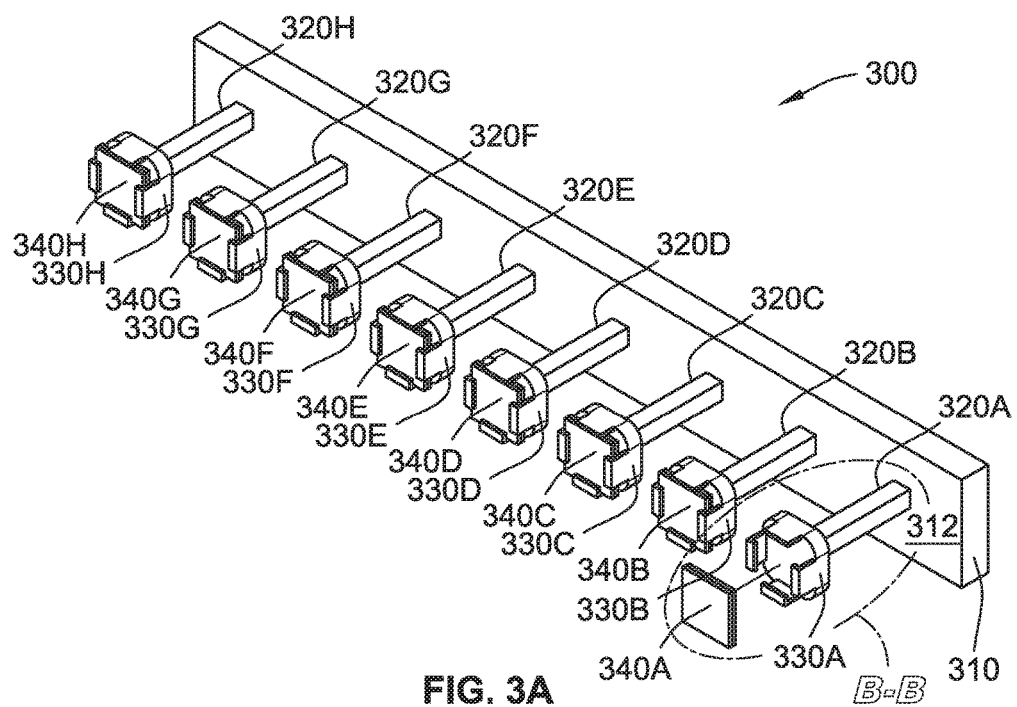
FIG. 3A is a perspective view of a sensor array of the system of FIG. 1 according to some implementations of the present disclosure.
Figure 3B:
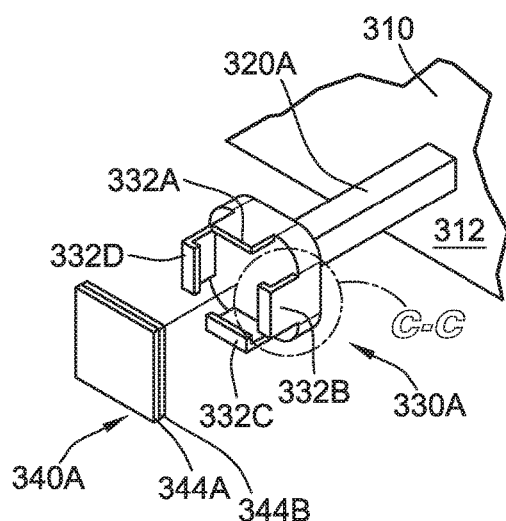
FIG. 3B is an enlarged perspective view of a mounting portion and sensor of the sensor array of FIG. 3A according to some implementations of the present disclosure.

Referring generally to FIGS. 3A and 3B, the sensor array 300 includes a base portion 310, a plurality of arm portions 320A-320H, a plurality of mounting portions 330A-330H, and a plurality of sensors 340A-340H. As shown in FIG. 3A, each of the plurality of arm portions 320A-320H are coupled to, and extend from, a lower surface 312 of the base portion 310. Each of the plurality of mounting portions 330A-330H are coupled to a corresponding one of the plurality of arm portions 320A-320H (e.g., first mounting portion 330A is coupled to first arm portion 320A) and configured to receive a corresponding one of the plurality of sensors 340A-340H (e.g., first sensor 340A is received by first mounting portion 330A).

The plurality of sensors 340A-340H are interferometric reflectance imaging sensors ("IRIS" or "IRI sensors"). IRI sensors can be manufactured on a silicon substrate in large quantities and are often used for high-throughput detection and quantification of protein-protein binding, DNA-protein binding, and DNA-DNA hybridization in real-time with high sensitivity and reproducibility. IRI sensors are multiplexed, meaning that each sensor can be used to test for a variety of tests. Each of the sensors 340A-340H includes a silicon dioxide layer and a silicon substrate. As shown in FIG. 3B, sensor 340A includes a silicon substrate 342A and a silicon dioxide layer 344A. Sensors 340B-340H include the same or similar silicon substrate and silicon dioxide layer as sensor 340A. As described in further detail herein, each of the sensors 340A-340H can be disposed within one of the wells of the microwell plate 200 containing a sample (FIG. 2B). The sensors 340A-340H can then be imaged by an objective and imaging device of the microscopy system 400 (FIG. 1) to determine an interference of light reflected from the sensor surface to identify nanoparticles and/or biomolecules within the sample. The sensors 340A-340H can be "spotted" with between about 100 spots and about 1,000 spots for testing. For example, each of the spots on the sensors 340A-340H can have a different binding agent.

As shown in FIG. 3B, mounting portion 330A includes a plurality of clip portions 332A-332D to aid in coupling sensor 340A to the mounting portion 330A. Mounting portions 330B-330H include the same or similar clip portions for aiding in coupling the corresponding sensor 340B-340H thereto. As shown, the first clip portion 332A has a generally rectangular shape. The second clip portion 332B, the third clip portion 332C, and the fourth clip portion 332D are independently moveable relative to the rest of the mounting portion 330A to aid in coupling the sensor 340A to the mounting portion 330A. More specifically, the second clip portion 332B, the third clip portion 332C, and the fourth clip portion 332D are generally biased towards the positions shown in FIG. 3B, however, these clip portions can be moved in a direction away from a center of the mounting portion 330A (or a central axis of the arm portion 320A) to allow the sensor 340A to be coupled thereto. By being generally biased towards the positions shown in FIG. 3B, the clip portions 332B-332D aid in securing the sensor 340A to the mounting portion 330A (e.g., such that the sensor 340A does not fall off when the sensor array 300 is moved).

Figure 3C:
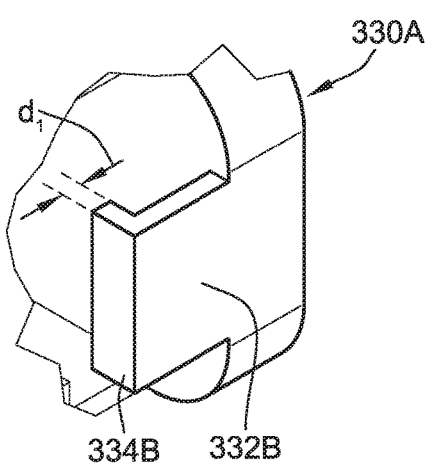
FIG. 3C is an enlarged perspective view of the mounting portion of FIG. 3B according to some implementations of the present disclosure.

The second clip portion 332B, the third clip portion 332C, and the fourth clip portion 332D each have a lip that aids in coupling the corresponding sensor to the mounting portion and also aids in positioning the sensor at a predetermined depth in the microwell plate 200. As shown in FIG. 3C, the lip 334B of the clip portion 332B has a predetermined thickness di. As described in further detail herein, the predetermined thickness of the lip 334B aids in positioning the corresponding sensor at a predetermined depth within one of the wells of the microwell plate 200. The predetermined thickness of the lip 334B can be adjusted based on the properties of the objective of the microscopy assembly 400 that is used to image the samples (e.g., the working distance of the objective). For example, in some implementations, the predetermined thickness of the lip 334B can be between about 0.1 mm and about 5 mm, between about 0.5 mm and about 3 mm, between about 1 mm and about 2 mm, etc. For the high-magnification imaging approaches described herein, the predetermined thickness of the lip 334B is preferably between about 100 microns and about 250 microns (e.g., such that a distance between the sample and the objective is between about 100 microns and about 250 microns). For the low-magnification imaging approaches described herein, the predetermined thickness of the lip 334B is preferably between about 500 microns and about 1 mm (e.g., such that a distance between the sample and the objective is between about 500 microns and about 1 mm). While the mounting portion 330A is shown in FIG. 3B as including three clip portions 332A-332D, more generally, the mounting portion 330A (and/or more generally any of the mounting portions 330A-330H) can have more or less clip portions (e.g., 2 clip portions that are the same as, or similar to, the first clip portion 332A and the third clip portion 332C, 2 clip portions that are the same as, or similar to, the second clip portion 332B and the fourth clip portion 332D, etc.)

While the plurality of sensors 340A-340D have been described herein as being coupled to the mounting portions 330A-330H via clip potions (e.g., clip portions 332A-332D), more generally, other coupling mechanisms for coupling the plurality of sensors 340A-340H to the mounting portions 330A-330H are contemplated. For example, in some implementations, the plurality of sensors 340A-340H can be coupled to the corresponding mounting portions 330A-330H via an adhesive connection. Moreover, while the plurality of sensors 340A-340H can be described herein as being removably coupled to the sensor array 300 (e.g., such that a first set of sensors can be replaced with a second set of sensors after use), in some implementations, the plurality of sensors 340A-340H can be permanently or fixedly attached to the sensor array 300 (e.g., via the mounting portions 330A-330H).

In some implementations, one or more of the sensors 340A-340H of the sensor array 340 include one or more protrusions that extend from an outer surface of the silicon dioxide layer. In such implementations, the sensor array 340 does not include the clip portions 332A-332D. The one or more protrusions have a predetermined length that is the same as, or similar to, the predetermined thickness d of the lip 334B (FIG. 3C) such that when the sensors 340A-340H having the one or more protrusions are disposed with the microwell plate 200, the sensors 340A-340H are positioned at a predetermined depth that is the same as, or similar to, the predetermined length of the one or more protrusions. Thus, in such implementations, the one or more protrusions aid in positioning the sensors 340A-340H at the predetermined depth. Alternatively, in other implementations in which the sensor array 340 does not include the clip portions 332A-332D, one or more of the wells in the microwell plate 200 (FIG. 2) (e.g., each of the wells) can include one or more protrusions extending upwardly from the glass plate 240 (FIG. 2B) having a predetermined length such that the one or more protrusions aid in positioning the sensors 340A-340H of the sensor array at the predetermined depth within the wells of the microwell plate 200. Alternatively still, in some implementations, one or more of the wells in the microwell plate 200 can include an insert (e.g., a gasket) that performs the same or similar function as the one or more protrusions (e.g., aids in positioning the sensors 340A-340H at the predetermined depth within the microwell plate 200).

While the sensor array 300 has been shown and described herein as having the same number of arm portions 320A-320H, mounting portions 330A-330H, and sensors 340A-340H as the number of wells in a single one of the rows 230A-230L (FIG. 2A) of the microwell plate 200 (e.g., each of which contains eight wells in the implementation shown in FIG. 2A), more generally, the sensor array 300 can have any suitable number of arm portions 320A-320H, mounting portions 330A-330H, and sensors 340A-340H. For example, in some implementations, the sensor array 300 includes the same number of arm portions 320A-320H, mounting portions 330A-330H, and sensors 340A-340H two or more of the rows 230A-230L of the microwell plate 200 (FIG. 2A). In such implementations, the sensor array 300 can be disposed in more than one row of the plurality of rows 230A-230L of the microwell plate 200 at a given time. Alternatively, in some implementations, the number of arm portions 320A-320H, mounting portions 330A-330H, and sensors 340A-340H in sensor array 300 can be less than the total number of wells in each individual row 230A-230L of the microwell plate 200 (FIG. 2A). For example, in such implementations, rather than the sensor array 300 being configured to be disposed within an entire row 230A-230L, the sensor array 300 can be disposed within a portion of an entire row 230A-230L (e.g., one well, two wells, three wells, . . . n wells).

Various imaging approaches may be used to perform imaging and detection of particles and/or biomolecules using one or more of the sensors 340A-340H described herein. In particular, low-magnification or high-magnification IRI imaging techniques, which are described in further detail herein, can be used to image and analyze one or more of the sensors 340A-340H.

Figure 4A:
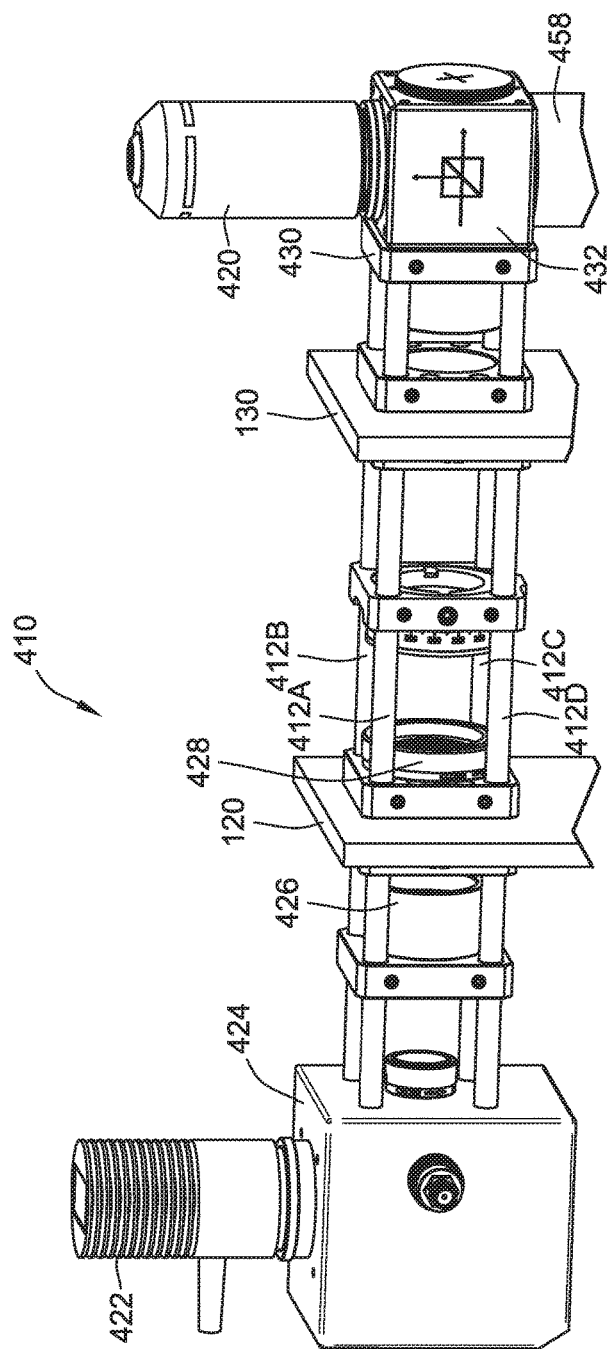
FIG. 4A is partial perspective view of the system of FIG. 1 including a first portion of a microscopy assembly according to some implementations of the present disclosure.
Figure 4B:
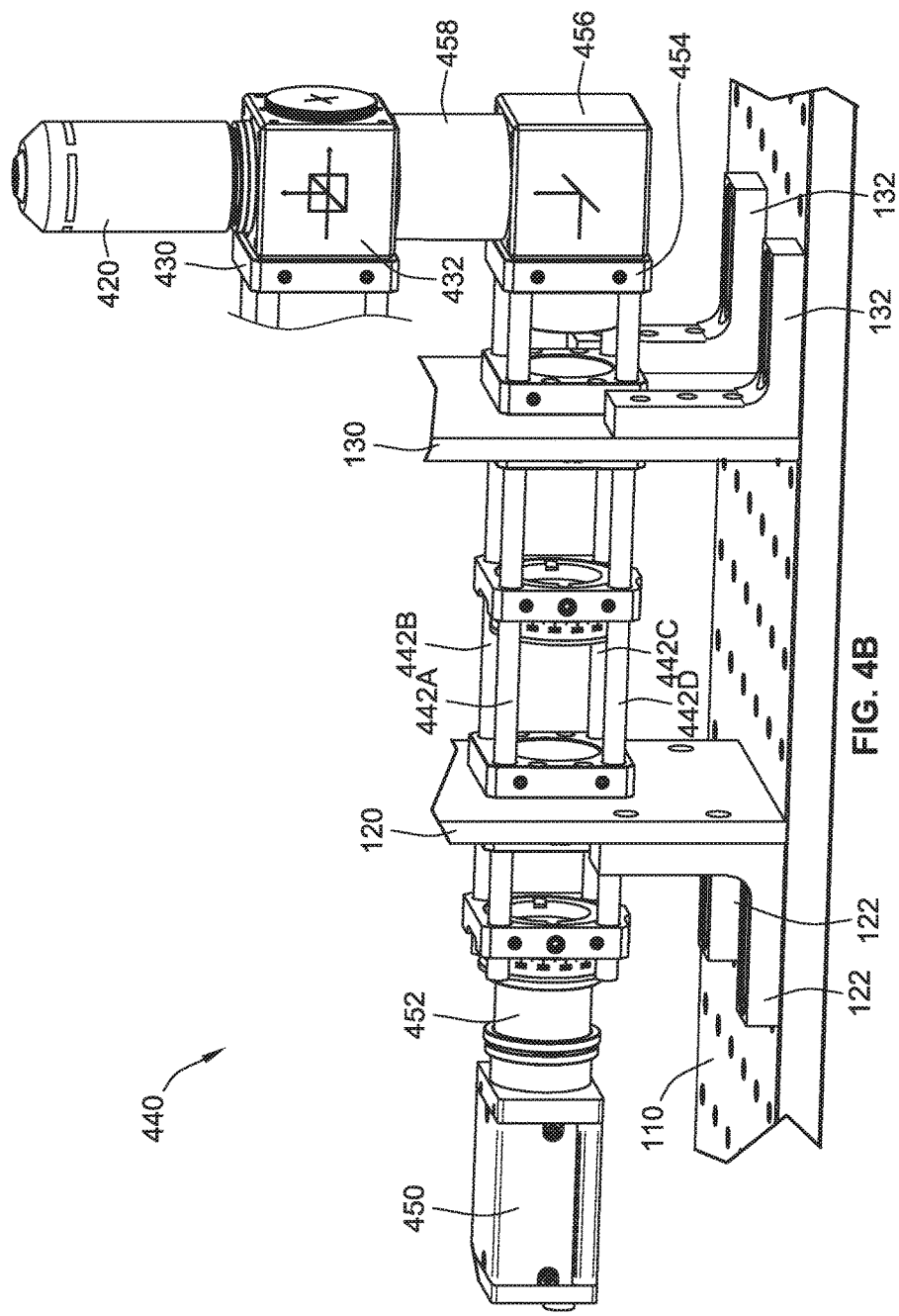
FIG. 4B is partial perspective view of the system of FIG. 1 including a second portion of the microscopy assembly according to some implementations of the present disclosure.

Referring generally to FIGS. 1, 4A, and 4B, the microscopy assembly 400 is generally used to image the plurality of sensors 340A-340H (FIG. 3A) to analyze liquid samples in the microwell plate 200 (FIG. 2A), as described in further detail herein. As shown in FIG. 1, the microscopy assembly 400 includes a first cage assembly 410 and a second cage assembly 440 for supporting the various components of the microscopy assembly 400.

Referring to FIG. 4A, the first cage assembly 410 includes a plurality of support rods 412A-412D that support an objective 420, an illumination source 422, an integrating sphere 424, a first lens 426, an iris diaphragm 428, a second lens 430, and a beamsplitter 432. As shown, the supporting rods 412A-412D extend through apertures in a first mounting plate 120 and a second mounting plate 130. As best shown in FIG. 1, the first mounting plate 120 is coupled to a base plate 110 of the system 100 via a pair of brackets 122. Similarly, the second mounting plate 130 is coupled to the base plate 110 via a pair of brackets 132.

The objective 420 of the microscopy assembly 400 is generally positioned below the microwell plate 200 (FIG. 1) such that one or more wells of the microwell plate 200 can be positioned within a field of view of the objective 420 (e.g., by moving the microwell plate 200 relative to the objective 420), as described in further detail herein. The objective 420 is used in conjunction with imaging device 450 and the illumination source 422 to capture one or more images. The illumination source 422 is used to light an object or area such that the imaging device 450 can obtain images via the objective 420. The illumination source 422 can be, for example, a LED light source, a fiber optic light source, or a florescent light source. Preferably, the illumination source 422 is an LED light source. As shown in FIG. 4A, the illumination source 422 is coupled to the first cage assembly 410 via an integrating sphere 424, which is in turn coupled directly to support rods 412A-412D. The integrating sphere 424 is generally used to evenly distribute light emitted by the illumination source 422 before reaching the objective 420.

The first lens 426 (FIG. 4A) is coupled to the support rods 412A-412D and is positioned between the illumination source 422 and the objective 420. The first lens 426 has a first focal length to aid in focusing light emitted from the illumination source 422 and integrating sphere 424 before reaching the objective 420. For example, the first lens 426 can have a focal length that is between about 10 mm and about 100 mm. Preferably, the focal length of the first lens 426 is about 30 mm. The iris diaphragm 428 (FIG. 4A) is coupled to the support rods 412A-412D and first mounting plate 120 and is generally used to selectively control the amount of light that reaches the objective 420. The second lens 430 (FIG. 4A) is the same as, or similar to, the first lens 426 is coupled to the support rods 412A-412D. The first lens 426 and the second lens 430 can have same or different focal lengths. For example, the second lens 430 can have a focal length of about 60 mm and the first lens can have a focal length of about 30 mm (e.g., a ratio of the focal length of the first lens 426 to the second lens 430 is 1:2).

The beamsplitter 432 is coupled to the second lens 430 and the support rods 412A-412D and is generally used to split incident light from the illumination source 422 into two, a first beam and a second beam, where the first beam is directed towards the objective 420. The first and second beams can have the same, or different, optical powers (e.g., the beamsplitter 432 directs 99% of the incident light towards the objective 420, directs 75% of the incident light towards the objective 420, directs 50% of the incident light towards the objective 420, directs 25% of the incident light towards the objective 420, directs 1% of the incident light towards the objective 420, etc.) As shown, the objective 420 is coupled to the beamsplitter 432 such that a field of view of the objective 420 is generally orthogonal to the support rods 412A-412D and the direction that incident light travels from the illumination source 422 through the first lens 426, iris diaphragm 428, and the second lens 430 before reaching the beamsplitter 432.

The objective 420 can have a magnification that is between about 4×-100× (e.g., 4×, 10×, 20×, 40×, 60×, 100×). For the low magnification imaging techniques described herein, the magnification of the objective 420 is preferably between about 1× and about 5×. For the high magnification imaging techniques described herein, the magnification of the objective 420 is preferably about 40×. The objective 420 can have a numerical aperture (often referred to by the acronym "NA") that is between about 0.1 and about 1.3 (e.g., 0.13, 0.3, 0.5, 0.75, 0.85, 1.25, 1.3). For the high magnification imaging techniques described herein, the numerical aperture (NA) of the objective 420 is preferably about 0.75. For the low magnification imaging techniques described herein, the numerical aperture (NA) of the objective 420 is preferably about 0.04. The objective 420 can have a working depth (often referred to by the acronym "WD") that is between about 0.15 mm and about 18 mm (e.g., about 0.2 mm, about 0.66 mm, about 2 mm, etc.) The working depth is the distance between the front edge of the objective and the specimen surface when the specimen is focused. The objective 420 also has a field of view that can be between about 100 microns and about 750 microns. For the high magnification imaging techniques described herein, the field of view, as measured along at least one dimension, can be at least about 100 microns (e.g., at least about 150 microns; e.g., at least about 200 microns; e.g., at least about 250 microns, e.g., at least about 350 microns). The size of the field of view can also be measured along an edge of the field of view (e.g., a side of a rectangular field of view) and/or along a diagonal (e.g., along a diagonal of a rectangular field of view). In the high magnification imaging techniques described herein, the field of view of the objective 420 is preferably between about 100 microns and about 350 microns.

Referring to FIG. 4B, the second cage assembly 440 of the microscopy assembly 400 includes a plurality of support rods 442A-442D that are the same as, or similar to, the support rods 412A-412D of the first cage assembly 410 (FIG. 4A) that are coupled to and/or support an imaging device 450, a first lens tube 452, a third lens 454, a turning mirror 456, and a second lens tube 458 of the microscopy assembly 400. The second lens tube 458 is positioned between and coupled to the beamsplitter 432 (which is in turn coupled to the objective 420) and the turning mirror 456. As light is reflected from the objective 420 through the beamsplitter 432, the second lens tube 458 allows this light to reach the turning mirror 456. The turning mirror 456 then redirects this light towards the imaging device 450 whose field of view is generally orthogonal to the field of view of the objective 420 (e.g., the field of view of the imaging device 450 is generally parallel to the support rods 442A-442D).

The turning mirror 456 is also coupled to the third lens 454 such that the light reflected towards the imaging device 150 passes through the third lens 454. The third lens 454 is the same as, or similar to, the first lens 426 and/or the second lens 430 that are coupled to the first cage assembly 410 (FIG. 4A). Preferably, the third lens 454 has the same focal length as the second lens 430 (FIG. 4A) (e.g., the third lens 454 has a focal of length of about 60 mm).

The imaging device 150 is coupled to the first lens tube 452 (which is turn coupled to the support rods 442A-442D). The imaging device 150 is configured to generate image data reproducible as one or more images of a sample within the field of view of the objective 420 (e.g., one or more images of one of the sensors 340A-340H (FIG. 3A) when disposed within the microwell plate 200). That is, the imaging device 150 receives light captured by the objective 420 that is directed towards the imaging device 150 via the turning mirror 456. The one or more images in the image data can include, for example, one or more fluorescence images, one or more label-free images, or any combination thereof. The imaging device 150 can be, for example, a charge-coupled device (CCD) sensor (camera). Alternatively, the imaging device 150 can be a complementary metal-oxide semiconductor (CMOS) sensor (camera).

In one non-limiting, exemplary implementation of the microscopy assembly 400, the illumination source 422 is a M660L4 Mounted LED manufactured by Thorlabs of Newton, N.J. (USA) ("Thorlabs"), the integrated sphere 424 is a IS200 Integrated Sphere manufactured by Thorlabs, the beamsplitter 432 is a CM1-BS013 beamsplitter manufactured by Thorlabs, the turning mirror 456 is a CM1-601 turning mirror manufactured by Thorlabs, the iris diaphragm 428 is a SM1D12D iris diaphragm manufactured by Thorlabs, the second lens 430 and the third lens 454 are AC254-060-A-ML lens manufactured by Thorlabs, the first lens 426 is an AC254-030-A-ML lens manufactured by Thorlabs, the first lens tube 452 is a SM1T10 lens tube manufactured by Thorlabs, the second lens tube 458 is a SC1L24 lens tube manufactured by Thorlabs, the imaging device 450 is a Grasshopper 2 Gig-E Vision camera manufactured by FLIR Integrated Imaging Solution of Richmond, BC (CA), and the objective 420 is a CFI Plan Flour 40× objective manufactured by Nikon.

Referring now to FIG. 5A, the linear translation stage assembly 500 includes a first linear translation stage 510, a second linear translation stage 530, and a z-stage assembly 560. The linear translation stage assembly 500 is generally used to move microwell plate 200 along an x-axis, a y-axis, a z-axis, or any combination thereof, to position on of the wells of the microwell plate 200 within the field of view of the objective 420 of the microscopy system 400 (FIG. 1).

Figure 5B:
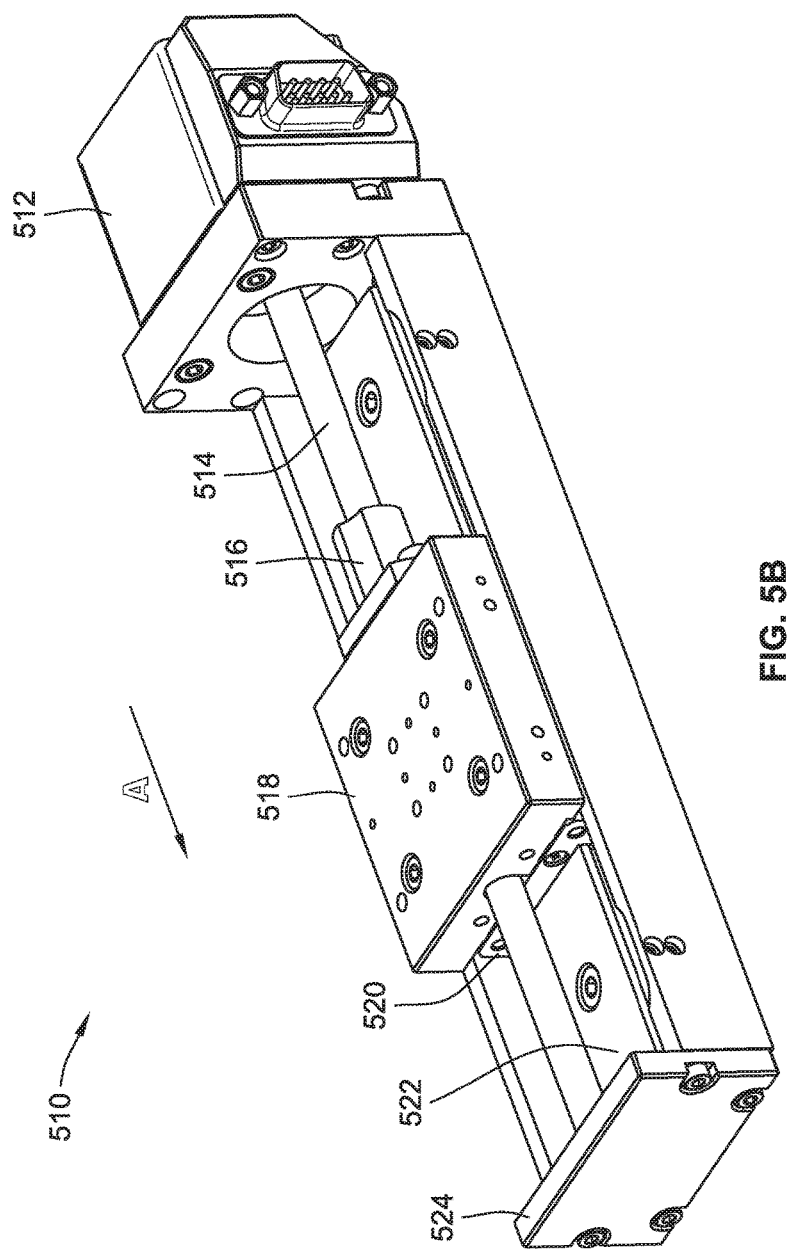
FIG. 5B is a perspective view of a first linear translation stage of the translation stage sub-assembly of FIG. 5A according to some implementations of the present disclosure.

Referring to FIG. 5B, the first linear translation stage 510 includes a motor 512, a lead screw 514, a nut 516, a carriage 518, a truck 520, a rail 522, and a housing 524. The carriage 518 can move in the direction of arrow A and/or or in the opposite direction of arrow A. Specifically, the lead screw 514 has male threads (e.g., a helical thread) and the nut 516 has female threads. The motor 512 causes rotation of the lead screw 514 (e.g., in a counterclockwise or clockwise direction), which in turn causes movement of the nut 516 due to the threaded connection between the lead screw 514 and the nut 516. The nut 516 is coupled to the carriage 518 and the truck 520, which in turn moves along the rail 522. As shown in FIG. 5C, the rail 522 is coupled to the housing 524 such that the rail 522 is stationary during rotation of the lead screw 514 and movement of the carriage 518 and truck 520. A portion of the truck 520 surrounds a portion of the rail 522 and is secured thereto via a tongue and groove connection. Thus, the truck 520 can move back and forth along the rail 522, which in turns causes movement of the carriage 518 responsive to the motor 512 rotating the lead screw 514.

Referring back to FIG. 5A, the second linear translation stage 530 is the same as, or similar to, the first linear translation stage 510. The housing 544 of the second linear translation stage 530 is coupled to the carriage 518 of the first linear translation stage 510 such that movement of the carriage 518 of the first linear translation stage 510 in either direction along the x-axis causes corresponding movement of the entire second linear translation stage 530. As shown, the lead screw 514 of the first linear translation stage 510 is generally orthogonal to the lead screw 534 of the second linear translation stage 530. As such, rotation of the lead screw 534 caused by the motor 535 causes movement of the carriage 538 of the second linear translation stage 530 in either direction along the y-axis. The carriage 538 of the second linear translation stage 530 is coupled to a platform block 550 (e.g., via fasteners) such that movement of the carriage 538 causes corresponding movement of the platform block 550. The platform block 550 is in turn coupled to the z-stage assembly 560. Thus, by causing movement of the carriage 518 along the x-axis, the first linear translation stage 510 causes corresponding movement of the microwell plate 200 in either direction along the x-axis. Likewise, by causing movement of the carriage 538 along the y-axis, the second linear translation stage 530 causes corresponding movement of the microwell plate 200 in either direction along the y-axis.

Figure 5D:
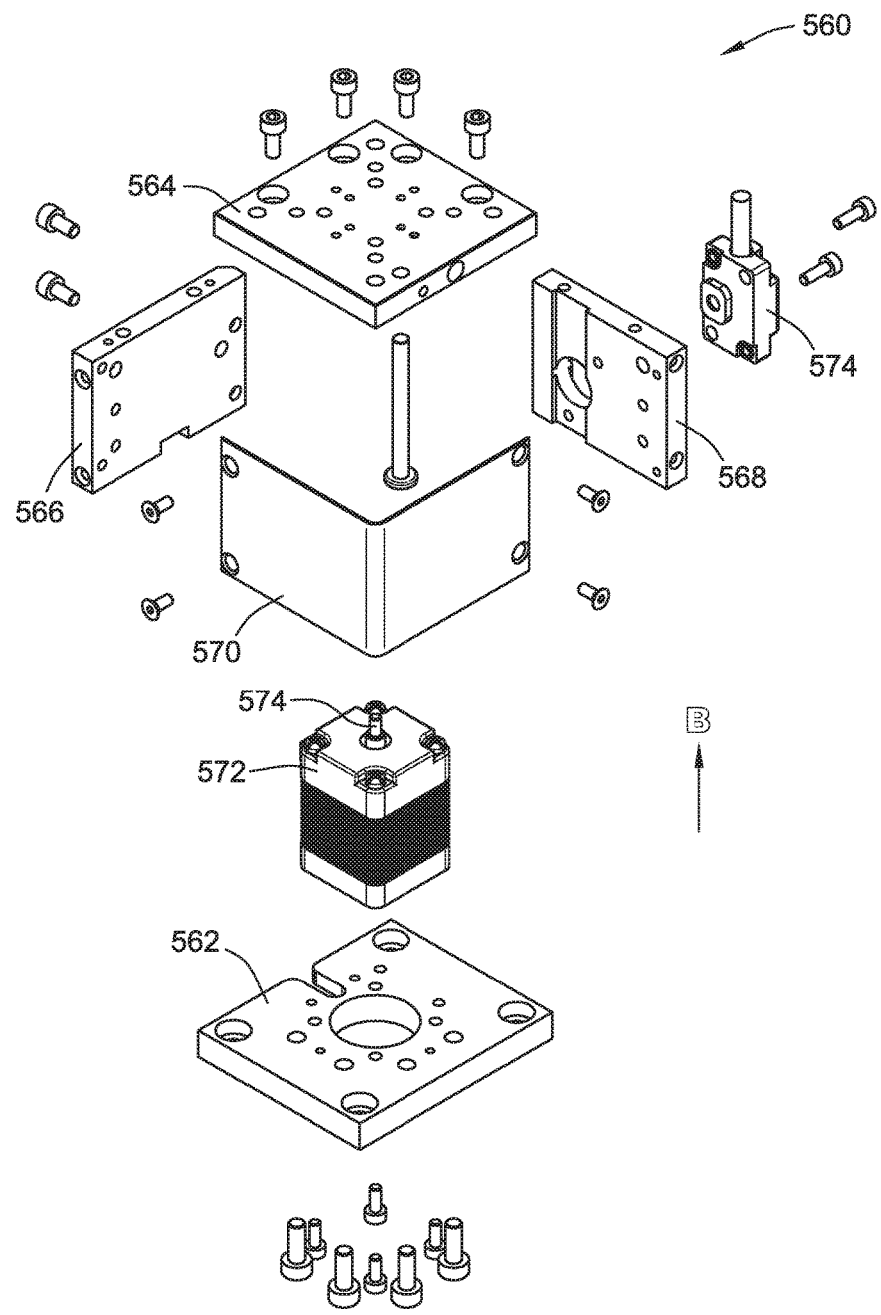
FIG. 5D is an exploded view of a z-stage actuator of the translation stage assembly of FIG. 5A according to some implementations of the present disclosure.

Referring to FIG. 5D, the z-stage assembly 560 includes a base plate 562, an upper plate 564, a first side wall 566, a second side wall 568, a side cover 570, a motor 572, and a lead screw 574, and an optical encoder 576. Generally, the z-stage assembly 560 is used to move the microwell plate 200 in either direction along the z-axis (FIG. 5A). More specifically, the base plate 562 is coupled to the platform block 550 (e.g., via fasteners). The first side wall 566, the second side wall 568, and the side cover 570 are coupled to the upper plate 564 (e.g., via fasteners). The optical encoder 576 is coupled to the second side wall 568 (e.g., via fasteners). The motor 572 is similar to the motor 512 of the first linear translation stage 510 (FIG. 5B) described herein in that the motor 572 causes rotation of lead screw 574 (e.g., in a clockwise or counterclockwise direction). Rotation of the lead screw 574 in a first rotational direction causes movement of the upper plate 564 (and the first side wall 566, the second side wall 568, and the side plate 570) in the direction of arrow B, while rotation of the lead screw 574 in a second rotational direction causes movement of the upper plate 564 in the opposite direction of arrow B. In this manner, the z-stage assembly 560 can move the microwell plate 200 (which is indirectly coupled to the z-stage assembly 560) in either direction along the z-axis (FIG. 5A).

Figure 5E:
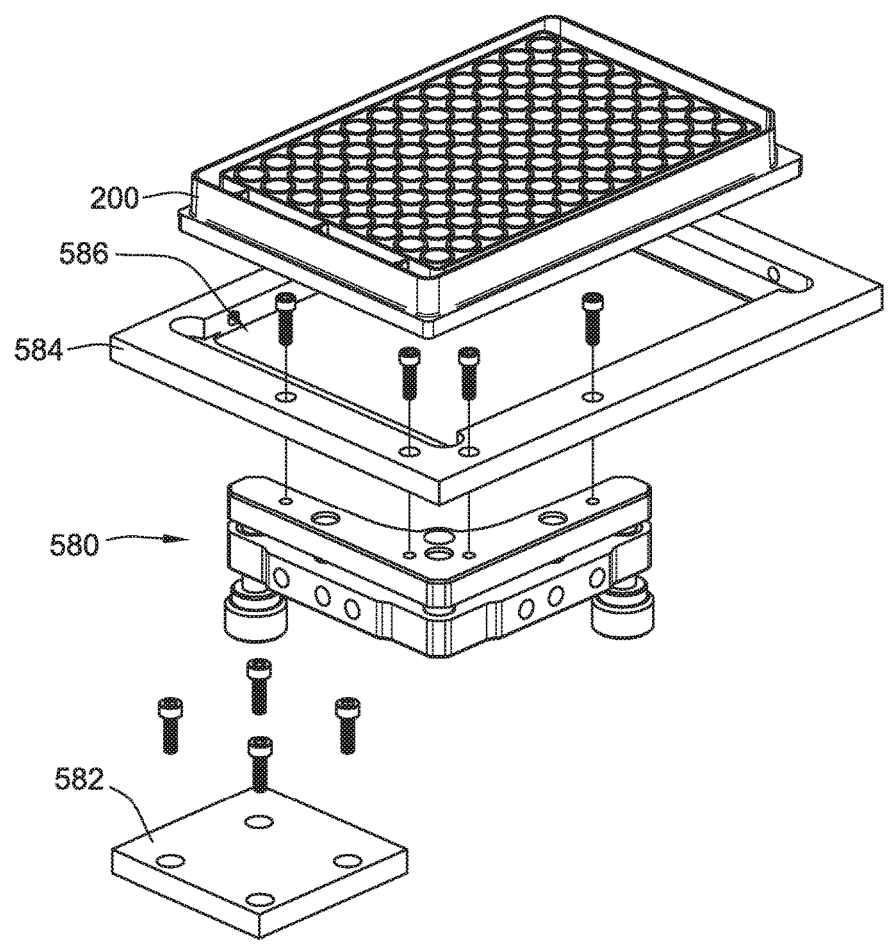
FIG. 5E is an exploded view of a kinematic platform mount and adapter plate of the translation stage assembly of FIG. 5A according to some implementations of the present disclosure.

Referring to FIG. 5A, the microwell plate 200 is coupled (indirectly) to the first linear translation stage 510, the second linear translation stage 530, and the z-stage assembly 560 via a mounting plate 582, a kinematic platform mount 580, and an adapter plate 584. The mounting plate 582 is coupled to the upper plate 564 of the z-stage assembly 560 (e.g., via fasteners). Referring to the exploded view of FIG. 5E, the kinematic platform mount 580 is coupled to the mounting plate 582 (e.g., via fasteners) and the adapter plate 584 (e.g., via fasteners). The kinematic platform mount 580 allows the microwell plate 200 (via the adapter plate 584) to repeatedly mount, remove, and replace the microwell plate 200 with high repeatability and precision. In one non-limiting, exemplary implementation, the kinematic platform mount 580 is a KM200B Kinematic Platform Mount manufactured by Thorlabs of Newton, N.J. (USA). The adapter plate 584 is generally used to couple the microwell plate 200 to the rest of the linear translation stage assembly 500 and includes an opening 586 that is sized and shaped to receive the microwell plate 200 therein such that the microwell plate 200 is removably coupled to the adapter plate 584.

Figure 6:
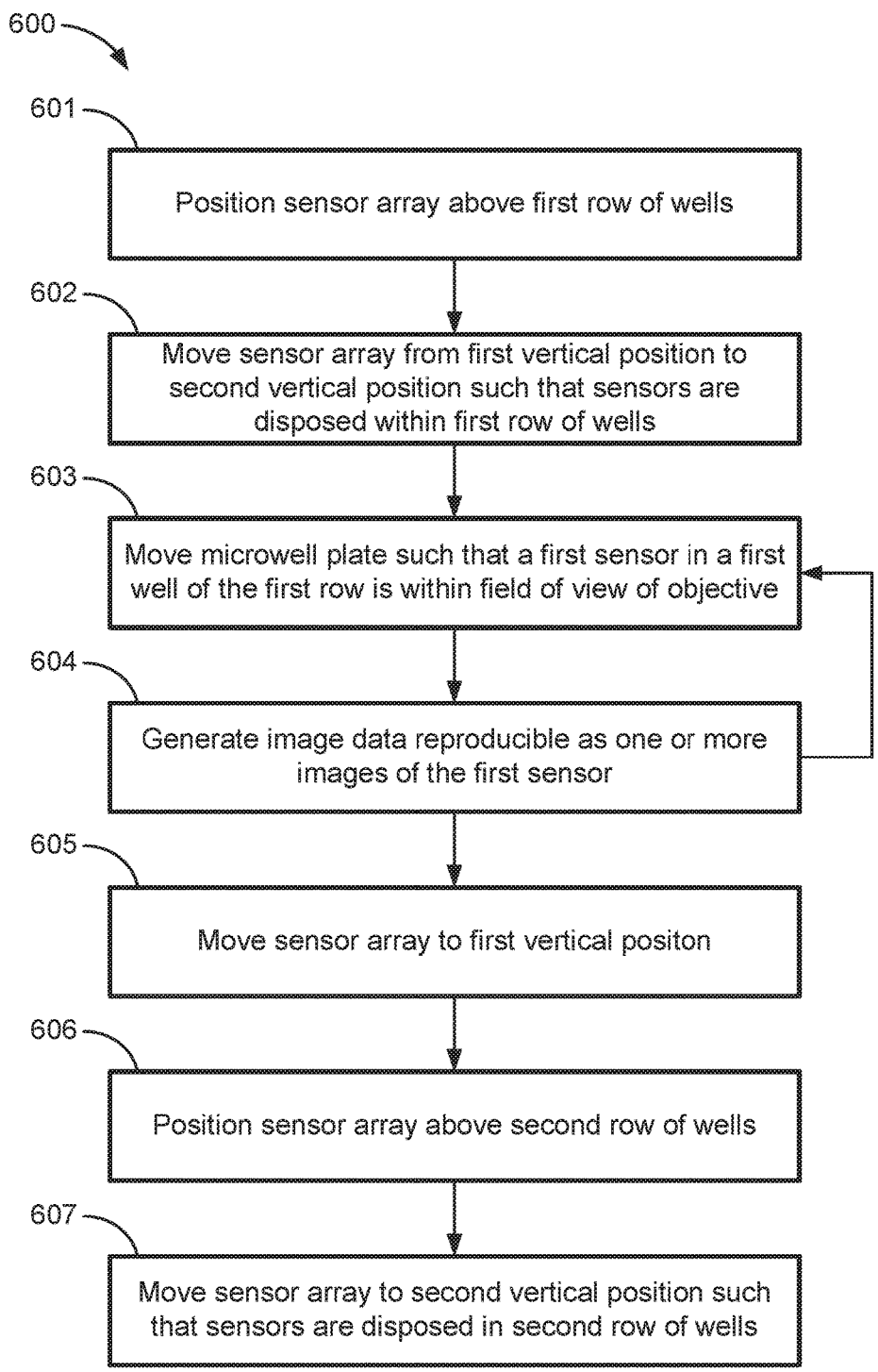
FIG. 6 is a process flow diagram for a method of imaging and analyzing one or more samples using the system of FIG. 1 according to some implementations of the present disclosure.

Referring to FIG. 6, a method 600 for imaging one or more samples (e.g., liquid samples) is shown. The method 600 can be implemented using a system that is the same as, or similar to, the system 100 described herein.

Figure 7:
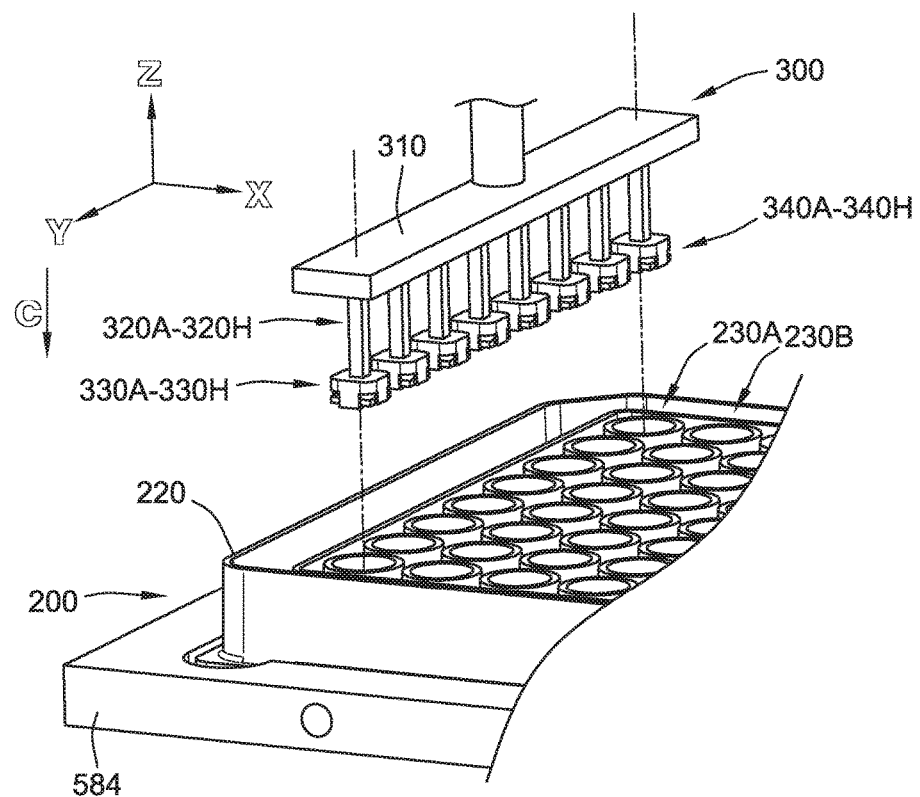
FIG. 7 a partial perspective view of the system of FIG. 1 with the sensor array in a first vertical position according to some implementations of the present disclosure.

Step 601 of the method 600 includes positioning the sensor array 300 above one of the plurality of rows 230A-230H of the microwell plate 200. Referring to FIG. 7, the sensor array 300 is positioned above the first row 230A of the plurality of rows of the microwell plate 200 in a first vertical position. In this first vertical position, the plurality of sensors 340A-340H of the sensor array 300 are positioned above the wells of the microwell plate 200, i.e., the sensors 340A-340H are not disposed within wells of the microwell plate 200 so that the sensor array 300 can freely move relative to the microwell plate 200. The sensor array 300 can be positioned as shown in FIG. 7 using a variety of methods and/or mechanisms. For example, the sensor array 300 can be manually positioned as shown in FIG. 7 (e.g., by a human user) or automatically positioned as shown in FIG. 7 (e.g., using a robotic arm that is coupled to the sensor array 300).

Figure 8:
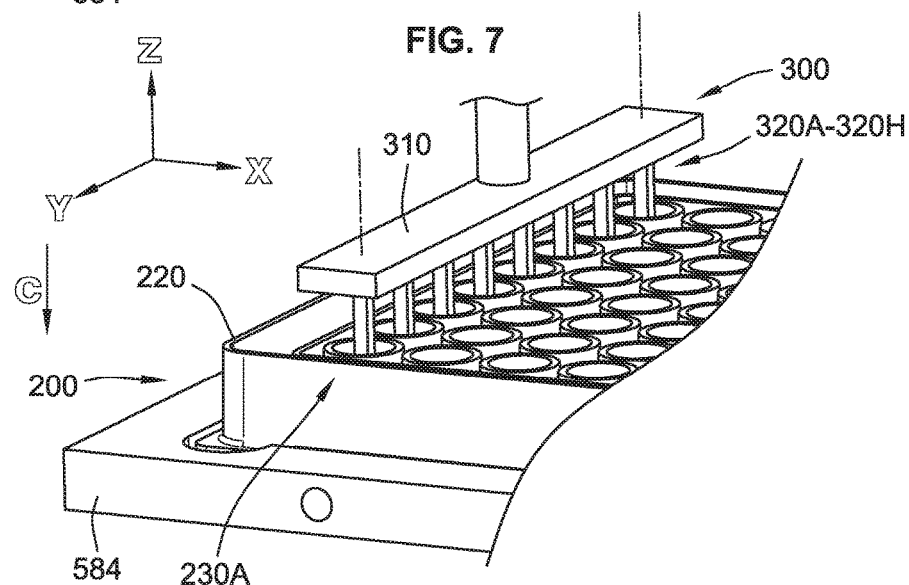
FIG. 8 a partial perspective view of the system of FIG. 1 with the sensor array in a second vertical position according to some implementations of the present disclosure.

Step 602 of the method 600 includes moving the sensor array 300 from the first vertical position (FIG. 7) to a second vertical position (FIG. 8) such that each of the plurality of sensors 340A-340H of the sensor array 300 are disposed within the first row 230A of the microwell plate 200. Specifically, the sensor array 300 is moved in the direction of arrow C (e.g., manually or automatically) until the sensors 340A-340H are disposed within the first row 230A at a predetermined depth. For example, referring to FIG. 9, first sensor 340A of the sensor array 300 is disposed within a first well of the first row 230A at a predetermined depth d. As shown, the predetermined depth d is substantially equal to the predetermined thickness of the lip 334B of the second clip portion 332B of the mounting portion 330A. In other words, the lip 334B contacts the glass plate 240 at the bottom of the well, and the predetermined thickness d of the lip 334B causes the sensor 340A to be disposed the predetermined depth. In this manner, the predetermined thickness d of the lip 334B can be selected to adjust the predetermined depth of the sensors 340A-340H.

Figure 9:
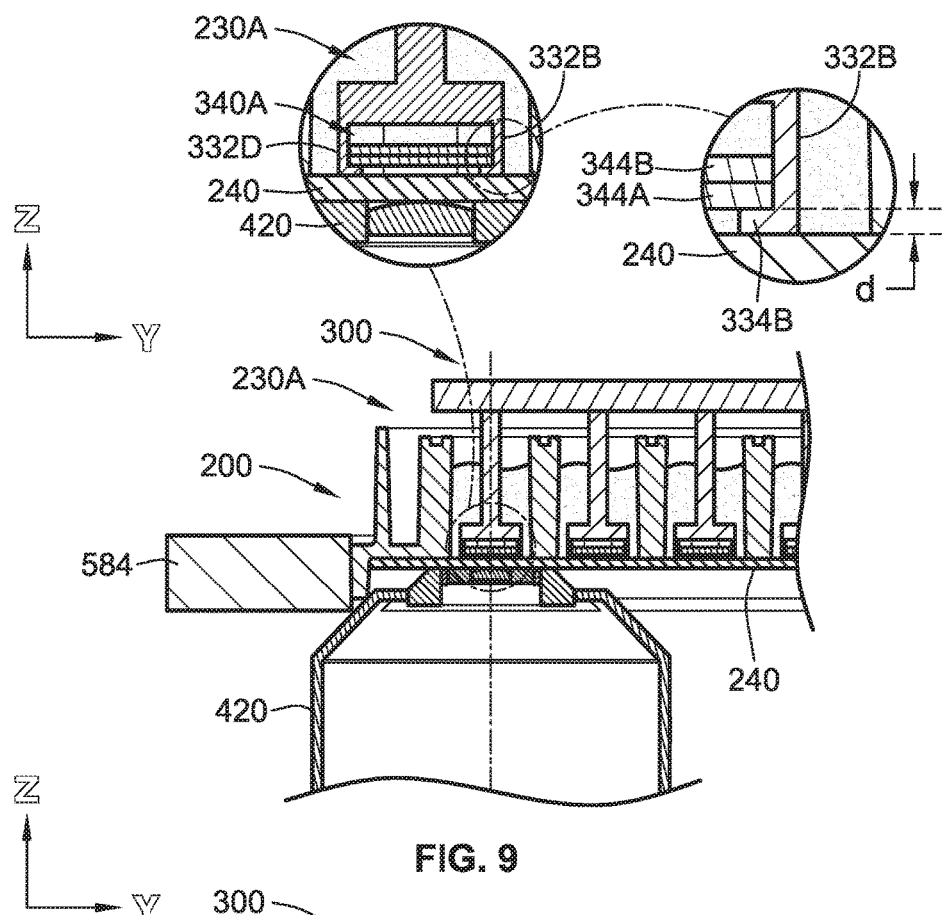
FIG. 9 is a partial cross-sectional view of the system of FIG. 1 with an objective positioned below a first sensor of the sensor array according to some implementations of the present disclosure.

Step 603 of the method 600 includes moving the microwell plate 200 (e.g., along the x-axis, the y-axis, or both using the linear translation stage assembly 500 described herein) relative to the objective 420 of the microscopy assembly 400 such that first sensor 340A is within the field of view of the objective 420. For example, as shown in FIG. 9, the first sensor 340A is within the field of view of the objective 420.

Step 604 of the method 600 includes generating image data reproducible as one or more images of the first sensor 340A using the imaging device 450 (FIG. 1) of the microscopy system 400. For example, the imaging device 450 can generate one image, two images, ten images, one hundred images, etc. of the first sensor 340A in the sample within the first well through the glass plate 240 of the microwell plate 200. Because the glass plate 240 has one or more predetermined properties, the objective 420 can be selected and/or calibrated to account for any refraction or absorption of light caused by the glass plate 240 of the microwell plate 200.

The image data generated by the imaging device 450 during step 604 can be transmitted (e.g., via a wireless connection or a wired connection) to one or more memory devices (e.g., that are part of the system 100 or external to the system 100) for later processing and analysis. Additionally or alternatively, the image data generated by the imaging device 450 during step 604 can be transmitted to a display device (e.g., monitor, LCD/LED screen, laptop, tablet, smartphone, etc.) such that a human user can view the images of the sensor 340A in substantially real-time.

Figure 10:
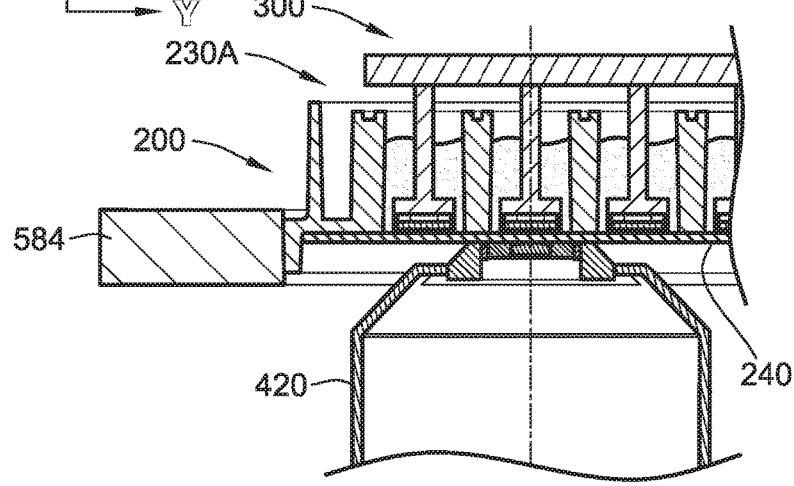
FIG. 10 is a partial cross-sectional view of the system of FIG. 1 with the objective positioned below a second sensor of the sensor array according to some implementations of the present disclosure.

After completing steps 603 and 604 of method 600 for the first sensor 340A in the first well of the first row 230A, steps 603 and 604 can be repeated for one or more of the wells in the first row 230A. For example, referring to FIGS. 9 and 10, after generating image data reproducible as one or more images of the first sensor 340A using the imaging device 450 during step 604, step 603 is repeated to move the microwell plate 200 relative to the objective 420 such that a second well containing the second sensor 340B is within the field of view of the objective 420. As shown by a comparison of FIGS. 4A and 4B, the objective 420 remains stationary while the microwell plate 200 is moved (e.g., using the linear translation stage assembly 500) along the y-axis. Step 604 is then repeated for the second sensor 340B such that the imaging device 450 generates image data reproducible as one or more images of the second sensor 340B.

In this manner, steps 603 and 604 are repeated to generate image data for all or some of the sensors 340A-340H in all of the wells in the first row 230A (e.g., all of sensors 340A-340H, only sensors 340A and 340B, sensors 340A-340C, sensors 340A and 340H, or any other combination of sensors 340A-340H). Alternatively, some implementations, steps 603 and 604 are not repeated such that the imaging device 450 only generates images data for one sensor in the first row 230A of the microwell plate 200 (e.g., only sensor 340A). Further, while steps 603 and 604 have been described herein as starting with first sensor 340A and then being repeated for second sensor 340B through 340H, more generally, the first instances of steps 603 and 604 can start with any one of the sensors 340A-340H disposed within the first row 230A of the microwell plate 200 (e.g., start with sensor 340D, move to sensor 340E, etc.)

Subsequent to obtaining image data for each of the desired sensors 340A-340H (e.g., all or some of the sensors 340A-340H) when disposed within the first row 230A of the microwell plate 200 as shown in FIGS. 7-10, the method 600 proceeds to step 605, which includes moving (e.g., manually or automatically) the sensor array 300 in the opposite direction of arrow C (FIG. 7) to the second vertical position (FIG. 7) such that the sensors 340A-340H are no longer disposed within the first rows 230A of the microwell plate 200.

Step 606 of the method 600 includes positioning the sensor array 300 above the second row 230B of the microwell plate in the same or similar manner as positioning the sensor array 300 above the first row 230A (FIG. 7) in step 601. Step 607 includes moving the microwell plate 200 relative to the objective 420 (e.g., along the x-axis, y-axis, or both) using the linear translation stage assembly 500 such that the first sensor 340A that is disposed within a first well of the second row 230B is within the field of view of the objective 420.

The method 600 further includes generating image data reproducible as one or more images or one or more of the sensors 340A-340H when disposed within the second row 230B of the microwell plate 200 in the same or similar manner as steps 603 and 604 described above. Further, the method 600 includes repeating steps 601-607 for all or some of the plurality of rows 230A-230L of the microwell plate 200 (FIG. 2A). Thus, the method 600 can include generating image data reproducible as one or more images of each of the sensors 340A-340H of the sensor array 300 when disposed within each of the rows 230A-230L of the microwell plate 200. In this manner, each sample within each well of the microwell plate 200 can be analyzed using the generated image data from the sensors 340A-340H.

While the steps of the method 600 have been described herein as being repeated such that the sensor array 300 is disposed within each of the plurality of rows of wells 230A-230L of the microwell plate 200, in some implementations of the method 600, the sensor array 300 is only disposed within some of the plurality of rows of wells 230A-230L (e.g., every other row, every two rows, every three rows, only rows 230A-230D, only rows 230D-230L, etc.)

In some implementations, the wells in the first row 230A include biological samples and the wells in the second row 230B include a buffer solution. In other words, every other one of the rows 230A-230L includes biological samples and buffer solutions. In such implementations, alternating between biological samples and buffer solutions is advantageous because the buffer solution aids in removing biological sample fluid from one row (e.g., row 230A) before the sensors 340A-340H are inserted into another row (e.g., row 230C). Without the buffer solution row, it is possible that the biological samples from one row could contaminate the samples in another row and cause inaccurate results when analyzing the image data.

In some implementations, the method 600 further includes analyzing the image data generated by the imaging device to analyze one or more properties of the samples within the microwell plate 200. Various imaging approaches may be used to perform imaging and detection of particles and/or biomolecules using one or more of the sensors 340A-340H described herein. In particular, low-magnification or high-magnification IRI imaging techniques can be used in accordance with the systems and methods described herein.

Low magnification IRI imaging uses a relatively low numerical aperture (NA) objective 420 to illuminate the surface of one of the sensors 340A-340H (e.g., IRI chip) and detect light reflected therefrom. The low NA objective 420 directs light to, and collects light reflected from, the surface of the IRI chip within a narrow cone of shallow angles (e.g., close to perpendicular to the surface of the IRI chip). Intensities of reflected light from the surface of the IRI chip are detected by the imaging device 450 vary with the wavelength, thus producing a characteristic spectral response that is a function of optical thickness (physical thickness and refractive index) of the $SiO_2$ layer of the IRI chip.

While other aspects are contemplated, this characteristic spectral response is believed to be produced by spectral interference between light reflected by the top, partially transmissive silicon dioxide ($SiO_2$) layer 344A (FIG. 3B) and light reflected by the silicon substrate 344B (FIG. 3B) beneath, which results in a sinusoidal variation in intensity with wavelength. By imaging the IRI surface at multiple wavelengths, this characteristic spectral response can be sampled. The IRI chip can be incubated in a sample, allowing biomolecules to bind to its surface. Accumulation of biomolecules at the IRI chip surface forms a biolayer that influences the aforementioned spectral interference, causing a shift in the characteristic spectral response. This shift can be measured, and used to infer an effective thickness of the bound biolayer and, accordingly, quantify amounts of captured biomolecules (e.g., proteins that are bound to the biolayer).

High-magnification IRI imaging utilizes a relatively high NA objective 420, for example equal to or greater than about 0.75, capable of imaging single particles. While other aspects are contemplated, high-magnification IRI imaging also relies on interferometric detection. In particular, contrast in high-magnification IRI images is based on interference between light scattered by the particle and directly reflected by the IRI substrate surface. In high-magnification IRI imaging, single particles can be resolved, counted, and sized based on the detected signal.

While the sensor array 300 has been described herein as moving between a first vertical position (FIG. 7) and a second vertical position (FIG. 8), alternatively (or additionally), in some implementations of the method 600, the microwell plate 200 is moved between a first vertical position and a second vertical position. In such implementations, the sensor array 300 is stationary and the microwell plate 200 is moved (e.g., using z-stage assembly 560) in the opposite direction of arrow C (FIGS. 7 and 8) to move the sensor array 300 in and out of the wells of the microwell plate 200.

Similarly, while the microwell plate 200 has been described herein as moving relative to the objective 420 along the x-axis and the y-axis using the linear translation stage assembly 500, in some implementations, the objective 420 is moveable relative to the microwell plate 200 (e.g., using a linear translation stage assembly that is the same as, or similar to, the linear translation stage assembly 500 described herein). In such implementations, the microwell plate 200 can be stationary.

While the system 100 has been described and shown herein as including one microscopy assembly 400 having one objective 420 and one imaging device 450, in some implementations, the system 100 can include multiple microscopy assemblies and/or multiple objectives and/or imaging devices that are the same as, or similar to, the microscopy assembly 400, objective 420, and/or imaging device 450. In such implementations, increasing the number of objectives and imaging devices allows for higher throughput because more than one sensor disposed within the microwell plate 200 can be imaged at a given time, thereby reducing the amount of time required to image and analyze every sample within the microwell plate 200.

While the present disclosure has been described with reference to one or more particular embodiments or implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations according to aspects of the present disclosure may combine any number of features from any of the implementations described herein.

Alternative Implementations

Implementation 1.

A system for imaging one or more samples includes a microwell plate including a plurality wells arranged in a plurality of rows, each of the plurality of wells having an upper opening and an opposing transparent lower surface, each of the plurality of wells being configured to store a sample therein, a sensor array including a plurality of sensors, the sensor array being moveable relative to the microwell plate along a first axis between a first position and a second position, each of the plurality of sensors being positioned within a corresponding well at a predetermined depth for at least one of the plurality of rows responsive to the sensor array being in the second position, an objective, an imaging device, and one or more linear translation stages configured to move the microwell plate relative to the objective along (i) a second axis, (ii) a third axis, or (iii) both (i) and (ii) to allow the imaging device to obtain image data reproducible as one or more images of each of the plurality of sensors.

Implementation 2.

The system according to implementation 1, wherein the sensor array includes a base portion, a plurality of arm portions, and a plurality of mounting portions, each of the plurality of arm portions having a first end coupled to the base portion and a second end coupled to a corresponding one of the plurality of mounting portions, each of the plurality of sensors being coupled to a corresponding one of the plurality of mounting portions.

Implementation 3.

The system according to implementation 2, wherein each of the plurality of mounting portions includes one or more moveable clips configured to aid in coupling each of the plurality of sensors to the corresponding one of the plurality of mounting portions.

Implementation 4.

The system according to implementation 3, wherein each of the one or more moveable arms includes a lip having a predetermined thickness corresponding to the predetermined depth, the lip aiding with disposing each of the plurality of sensors within the corresponding well at the predetermined depth.

Implementation 5.

The system according to any one of implementations 1-4, wherein the one or more linear translation stages includes (i) a first linear translation stage configured to move the microwell plate relative to the objective along the second axis and (ii) a second linear translation stage configured to move the microwell plate relative to the objective along the third axis.

Implementation 6.

The system according to implementation 5, wherein the one or more linear translation stages includes a third linear translation stage configured to move the microwell plate relative to the objective along the first axis.

Implementation 7.

The system according to any one of implementations 1-6, wherein the first axis is (i) orthogonal to the second axis and (ii) orthogonal to the third axis.

Implementation 8.

The system according to any one of implementations 1-7, wherein the objective is moveable along the first axis relative to the microwell plate.

Implementation 9.

The system according to any one of implementations 1-8, wherein the plurality of sensors includes interferometric reflectance imaging (IRI) sensors.

Implementation 10.

The system according to any one of implementations 1-9, wherein the imaging device is a charge-coupled device (CCD) sensor or a complementary metal-oxide semiconductor (CMOS) sensor.

Implementation 11.

The system according to any one of implementations 1-10, further comprising a first cage assembly coupled to and supporting a first plurality of lens, an iris diaphragm, a beamsplitter, an integrated sphere, and an illumination source, and a second cage assembly coupled to and supporting a second plurality of lens, a turning mirror, and the imaging device, the beamsplitter being positioned between the illumination source and the objective, the turning mirror being positioned between the imaging device and the objective.

Implementation 12.

The system according to any one of implementations 1-11, wherein the objective has a magnification of at least 40×, a numerical aperture of at least 0.75, a field of view of at least 100 microns, or any combination thereof.

Implementation 13.

The system according to any one of implementations 1-12, wherein the objective has a magnification of at least 1×, a numerical aperture of at least 0.04, a field of view of at least 5 mm, or any combination thereof.

Implementation 14.

The system according to any one of implementations 1-13, wherein the plurality of rows of wells of the microwell plate are arranged in a matrix with a first row of the matrix having a first number of wells that is a multiple of two and a second row that is orthogonal to the first row of the matrix having a second number of wells that is a multiple of three.

Implementation 15.

A system for analyzing one or more liquid samples includes a microwell plate including a plurality of rows of wells configured to store liquid samples, a sensor array that is moveable relative to the microwell plate along a first axis between a first position and a second position to allow a portion of the sensor array to be disposed within a first one of the plurality of rows of wells when the sensor array is in the second position, an objective, and one or more linear translation stages configured to move the microwell plate relative to the objective (i) along a second axis that is orthogonal to the first axis, (ii) along a third axis that is orthogonal to the first axis and the second axis, or (iii) both (i) and (ii).

Implementation 16.

The system according to implementation 15, wherein the sensor array includes a base portion, a plurality of arm portions, and a plurality of mounting portions for coupling a plurality of sensors to the sensor array, each of the plurality of arm portions having a first end coupled to the base portion and a second end coupled to a corresponding one of the plurality of mounting portions.

Implementation 17.

The system according to any one of implementations 15 and 16, further comprising a first cage assembly coupled to and supporting an illumination source, a beamsplitter, and the objective, and a second cage assembly coupled to and supporting an imaging device and a turning mirror.

Implementation 18.

A method for imaging one or more liquid samples disposed in a microwell plate includes moving a sensor array including a plurality of sensors from a first vertical position towards a second vertical position such that each of the plurality of sensors is disposed within a corresponding well in a first row of wells of the microwell plate, moving, using one or more linear translation stages, the microwell plate such that a first one of the plurality of sensors is positioned within a field of view of an objective, generating, using the objective and an imaging device, first image data reproducible as one or more images of the first sensor, moving, using the one or more linear translation stages, the microwell plate such that a second one of the plurality of sensors is positioned within the field of view of the objective, and generating, using the objective and the imaging device, second image data reproducible as one or more images of the second sensor.

Implementation 19.

The method according to implementation 18, further comprising identifying one or more nanoparticles on the first sensor based on the first image data and identifying one or more nanoparticles on the second sensor based on the second image data.

Implementation 20.

The method according to implementations 18 or 19, further comprising determining a thickness of a biolayer on the first sensor based on the first image data, determining a thickness of a biolayer on the second sensor based on the second image data, or both.

Implementation 21.

The method according to any one of implementations 18-20, wherein the first sensor is disposed within a first well of the microwell plate and the second sensor is disposed within a second well of the microwell plate, the first well including one or more target species, the second well including a control solution and does not include the one or more target species.

Implementation 22.

The method according to any one of implementations 18-21, further comprising moving the sensor array from the second vertical position towards the first vertical position such that each of the plurality of sensors is no longer disposed within the first row of wells of the microwell plate, moving, using the one or more translation stages, the microplate such that the sensor array is positioned above a second row of wells of the microwell plate, moving the sensor array from the first vertical position to the second vertical position such that each of the plurality of sensors is disposed within a well of the second row of wells.

Implementation 23.

The method according to implementation 22, wherein each well in the first row of wells includes a liquid sample and each well in the second row of wells includes a wash solution.

Implementation 24.

The method according to any one of implementations 18-23, wherein (i) the one or more images of the first sensor include a fluorescence image, a label-free image, or both and (ii) the one or more images of the second sensor include a fluorescence image, a label-free image, or both.

It is contemplated that any element or any portion thereof from any of implementations 1-24 above can be combined with any other element or elements or portion(s) thereof from any of implementations 1-24 to form an implementation of the present disclosure.

What is claimed is:

1. A system for imaging one or more samples, the system comprising:
   a microwell plate including a plurality wells arranged in a plurality of rows, each of the plurality of wells having an upper opening and an opposing transparent lower surface, each of the plurality of wells being configured to store a sample therein;
   a sensor array including a plurality of sensors, the sensor array being moveable relative to the microwell plate along a first axis between a first position and a second position, each of the plurality of sensors being positioned within a corresponding well at a predetermined depth for at least one of the plurality of rows responsive to the sensor array being in the second position;
   an objective;
   an imaging device; and
   one or more linear translation stages configured to move the microwell plate relative to the objective along (i) a second axis, (ii) a third axis, or (iii) both (i) and (ii) to allow the imaging device to obtain image data reproducible as one or more images of each of the plurality of sensors.

2. The system of claim 1, wherein the sensor array includes a base portion, a plurality of arm portions, and a plurality of mounting portions, each of the plurality of arm portions having a first end coupled to the base portion and a second end coupled to a corresponding one of the plurality of mounting portions, each of the plurality of sensors being coupled to a corresponding one of the plurality of mounting portions.

3. The system of claim 2, wherein each of the plurality of mounting portions includes one or more moveable clips configured to aid in coupling each of the plurality of sensors to the corresponding one of the plurality of mounting portions.

4. The system of claim 3, wherein each of the one or more moveable arms includes a lip having a predetermined thickness corresponding to the predetermined depth, the lip aiding with disposing each of the plurality of sensors within the corresponding well at the predetermined depth.

5. The system of claim 1, wherein the one or more linear translation stages includes (i) a first linear translation stage configured to move the microwell plate relative to the objective along the second axis and (ii) a second linear translation stage configured to move the microwell plate relative to the objective along the third axis.

6. The system of claim 5, wherein the one or more linear translation stages includes a third linear translation stage configured to move the microwell plate relative to the objective along the first axis.

7. The system of claim 1, wherein the first axis is (i) orthogonal to the second axis and (ii) orthogonal to the third axis.

8. The system of claim 1, wherein the objective is moveable along the first axis relative to the microwell plate.

9. The system of claim 1, wherein the plurality of sensors includes interferometric reflectance imaging (IRI) sensors.

10. The system of claim 1, wherein the imaging device is a charge-coupled device (CCD) sensor or a complementary metal-oxide semiconductor (CMOS) sensor.

11. The system of claim 1, further comprising:
a first cage assembly coupled to and supporting a first plurality of lens, an iris diaphragm, a beamsplitter, an integrated sphere, and an illumination source; and
a second cage assembly coupled to and supporting a second plurality of lens, a turning mirror, and the imaging device,
the beamsplitter being positioned between the illumination source and the objective, the turning mirror being positioned between the imaging device and the objective.

12. The system of claim 1, wherein the objective has a magnification of at least 40×, a numerical aperture of at least 0.75, a field of view of at least 100 microns, or any combination thereof.

13. The system of claim 1, wherein the objective has a magnification of at least 1×, a numerical aperture of at least 0.04, a field of view of at least 5 mm, or any combination thereof.

14. The system of claim 1, wherein the plurality of rows of wells of the microwell plate are arranged in a matrix with a first row of the matrix having a first number of wells that is a multiple of two and a second row that is orthogonal to the first row of the matrix having a second number of wells that is a multiple of three.

15. A system for analyzing one or more samples, the system comprising:
a microwell plate including a plurality of rows of wells configured to store samples;
a sensor array that is moveable relative to the microwell plate along a first axis between a first position and a second position to allow a portion of the sensor array to be disposed within a first one of the plurality of rows of wells when the sensor array is in the second position;
an objective; and
one or more linear translation stages configured to move the microwell plate relative to the objective (i) along a second axis that is orthogonal to the first axis, (ii) along a third axis that is orthogonal to the first axis and the second axis, or (iii) both (i) and (ii).

16. The system of claim 15, wherein the sensor array includes a base portion, a plurality of arm portions, and a plurality of mounting portions for coupling a plurality of sensors to the sensor array, each of the plurality of arm portions having a first end coupled to the base portion and a second end coupled to a corresponding one of the plurality of mounting portions.

17. The system of claim 15, further comprising
a first cage assembly coupled to and supporting an illumination source, a beamsplitter, and the objective; and
a second cage assembly coupled to and supporting an imaging device and a turning mirror.

18. A method for imaging one or more liquid samples disposed in a microwell plate, the method comprising:
moving a sensor array including a plurality of sensors from a first vertical position towards a second vertical position such that each of the plurality of sensors is disposed within a corresponding well in a first row of wells of the microwell plate;
moving, using one or more linear translation stages, the microwell plate such that a first one of the plurality of sensors is positioned within a field of view of an objective;
generating, using the objective and an imaging device, first image data reproducible as one or more images of the first sensor;
moving, using the one or more linear translation stages, the microwell plate such that a second one of the plurality of sensors is positioned within the field of view of the objective; and
generating, using the objective and the imaging device, second image data reproducible as one or more images of the second sensor.

19. The method of claim 18, further comprising identifying one or more nanoparticles on the first sensor based on the first image data and identifying one or more nanoparticles on the second sensor based on the second image data.

20. The method of claim 18, further comprising determining a thickness of a biolayer on the first sensor based on the first image data, determining a thickness of a biolayer on the second sensor based on the second image data, or both.

21. The method of claim 18, wherein the first sensor is disposed within a first well of the microwell plate and the second sensor is disposed within a second well of the microwell plate, the first well including one or more target species, the second well including a control solution and does not include the one or more target species.

22. The method of claim 18, further comprising
moving the sensor array from the second vertical position towards the first vertical position such that each of the plurality of sensors is no longer disposed within the first row of wells of the microwell plate;
moving, using the one or more translation stages, the microplate such that the sensor array is positioned above a second row of wells of the microwell plate;
moving the sensor array from the first vertical position to the second vertical position such that each of the plurality of sensors is disposed within a well of the second row of wells.

23. The method of claim 22, wherein each well in the first row of wells includes a liquid sample and each well in the second row of wells includes a buffer solution.

24. The method of claim 18, wherein (i) the one or more images of the first sensor include a fluorescence image, a label-free image, or both and (ii) the one or more images of the second sensor include a fluorescence image, a label-free image, or both.

* * * * *

UNITED STATES PATENT AND TRADEMARK OFFICE
CERTIFICATE OF CORRECTION

PATENT NO. : 10,585,042 B2
APPLICATION NO. : 16/432376
DATED : March 10, 2020
INVENTOR(S) : Unlü et al.

Page 1 of 1

It is certified that error appears in the above-identified patent and that said Letters Patent is hereby corrected as shown below:

In the Claims

At Column 18, Line 26 (Claim 1, Line 3), please delete "a microwell plate including a plurality wells arranged in" and insert --a microwell plate including a plurality of wells arranged in-- therefor.

Signed and Sealed this
Sixteenth Day of June, 2020

Andrei Iancu
*Director of the United States Patent and Trademark Office*